(12) United States Patent
Poydenot et al.

(10) Patent No.: US 12,303,498 B2
(45) Date of Patent: May 20, 2025

(54) ALK5 INHIBITORS AS SKELETAL MUSCLE HYPERTROPHY INDUCERS

(71) Applicant: CYTOO, Grenoble (FR)

(72) Inventors: Pauline Poydenot, Novalaise (FR); Joris Michaud, Lausanne (CH); Mélanie Flaender, Grenoble (FR); Eve Duchemin-Pelletier, Vizille (FR); Luc Selig, Charenton le Pont (FR)

(73) Assignee: CYTOO, Grenoble (FR)

( * ) Notice: Subject to any disclaimer, the term of this patent is extended or adjusted under 35 U.S.C. 154(b) by 0 days.

(21) Appl. No.: 16/982,607

(22) PCT Filed: Mar. 25, 2019

(86) PCT No.: PCT/EP2019/057426
§ 371 (c)(1),
(2) Date: Sep. 21, 2020

(87) PCT Pub. No.: WO2019/180269
PCT Pub. Date: Sep. 26, 2019

(65) Prior Publication Data
US 2021/0015807 A1    Jan. 21, 2021

(30) Foreign Application Priority Data

Mar. 23, 2018  (EP) .................................. 18305331

(51) Int. Cl.
*A61K 31/444*    (2006.01)
*A61K 31/4439*   (2006.01)
(Continued)

(52) U.S. Cl.
CPC ........ *A61K 31/444* (2013.01); *A61K 31/4439* (2013.01); *A61K 31/4709* (2013.01);
(Continued)

(58) Field of Classification Search
CPC ............ A61K 31/4375; A61K 31/4439; A61K 31/444; A61K 31/4709; A61K 31/496;
(Continued)

(56) References Cited

U.S. PATENT DOCUMENTS

2004/0063949 A1* 4/2004 Gellibert .................. A61P 1/16
                                                        546/122
2014/0127228 A1   5/2014 Marks et al.
(Continued)

FOREIGN PATENT DOCUMENTS

WO   WO-2008006583 A1 *  1/2008  ........... C07D 401/14
WO   WO 2008/052734         5/2008
(Continued)

OTHER PUBLICATIONS

Backman et. al., Neuromusc. Dis., vol. 5(3), pp. 233-241, publ. 1995 (Year: 1995).*

(Continued)

*Primary Examiner* — Sarah Pihonak
(74) *Attorney, Agent, or Firm* — SALIWANCHIK, LLOYD & EISENSCHENK

(57) ABSTRACT

The present invention relates to ALK5 inhibitors and their uses as skeletal muscle hypertrophy inducers as well as to promote skeletal muscle regeneration, to prevent skeletal muscle atrophy, or in the treatment or prevention of a disease or injury resulting in loss of skeletal muscle tissue and/or muscle weakness. It further relates to the non-therapeutic use of such compounds to increase muscle mass, muscle strength and/or muscle performance in a subject.

5 Claims, 6 Drawing Sheets

(51) Int. Cl.
  *A61K 31/4709* (2006.01)
  *A61K 31/498* (2006.01)
  *A61K 31/519* (2006.01)
  *A61K 31/573* (2006.01)
  *A61K 45/06* (2006.01)
  *A61P 21/00* (2006.01)

(52) U.S. Cl.
  CPC .......... *A61K 31/498* (2013.01); *A61K 31/519* (2013.01); *A61K 31/573* (2013.01); *A61K 45/06* (2013.01); *A61P 21/00* (2018.01)

(58) Field of Classification Search
  CPC .. A61K 31/498; A61K 31/517; A61K 31/519; A61K 31/56; A61K 31/573; A61K 31/58; A61K 45/06; A61P 21/00
  See application file for complete search history.

(56) References Cited

U.S. PATENT DOCUMENTS

| 2015/0175962 A1 | 6/2015 | Zhu et al. |
| 2020/0354680 A1 | 11/2020 | Dai et al. |

FOREIGN PATENT DOCUMENTS

| WO | WO-2009087225 A2 * | 7/2009 | ........... C07D 471/04 |
| WO | WO-2010102267 A2 * | 9/2010 | ......... A61K 31/4709 |
| WO | WO-2014201133 A1 * | 12/2014 | ............. A61K 35/30 |
| WO | WO-2016025629 A1 * | 2/2016 | ........... A61K 31/444 |
| WO | WO 2016/161192 | 10/2016 | |
| WO | WO 2017/027280 | 2/2017 | |
| WO | WO-2017120523 A2 * | 7/2017 | ......... A61K 39/3955 |
| WO | WO 2017/149025 | 9/2017 | |
| WO | WO 2017/177050 | 10/2017 | |

OTHER PUBLICATIONS

Trouth et. al., Autoimmune Dis., vol. 2012, pp. 1-11, publ. 2012 (Year: 2012).*
Fenichel, G. M. et al. "Long-term benefit from prednisone therapy in Duchenne muscular dystrophy" *Neurology*, Dec. 1991, pp. 1874-1877, vol. 41, No. 12.
Jude, B. et al. "Inhibition of TGF-β pathway protects diaphragm from both muscle atrophy and weakness during chronic sepsis" *Journal of Cachexia, Sarcopenia and Muscle*, 2017, Article No. 3-17, pp. 1034-1035, vol. 8, No. 6.
Ohsawa, Y. et al. "An inhibitor of transforming growth factor beta type I receptor ameliorates muscle atrophy in a mouse model of caveolin 3-deficient muscular dystrophy" *Laboratory Investigation*, Aug. 2012, pp. 1100-1114, vol. 92, No. 8.
Sandor, K. P. et al. "The effects of repsox on induced motor neuron survival during direct reprogramming" *Neuroscience 2012, 42$^{nd}$ Annual Meeting of the Society for Neuroscience*, 2012, p. 1, Abstract only.
Written Opinion in International Application No. PCT/EP2019/057426, May 2, 2019, pp. 1-7.
McDonald, C. M. et al. "Long-term effects of glucocorticoids on function, quality of life, and survival in patients with Duchenne muscular dystrophy: a prospective cohort study" *Lancet*, published online Nov. 22, 2017, pp. 451-461, vol. 391.
Tan, S. M. et al. "Targeted inhibition of activin receptor-like kinase 5 signaling attenuates cardiac dysfunction following myocardial infarction" *American Journal of Physiology-Heart and Circulatory Physiology*, Feb. 12, 2010, pp. H1415-H1425, vol. 298.
Gellibert, F. et al. "Discovery of 4-{4-[3-(Pyridin-2-yl)-1H-pyrazol-4-yl]pyridin-2-yl}-N-(tetrahydro-2H-pyran-4-yl)benzamide (GW788388): A Potent, Selective, and Orally Active Transforming Growth Factor-β Type I Receptor Inhibitor" *Journal of Medicinal Chemistry*, published on web Mar. 16, 2006, pp. 2210-2221, vol. 49, No. 7.

* cited by examiner

ALK5 INHIBITORS AS SKELETAL MUSCLE HYPERTROPHY INDUCERS

CROSS-REFERENCE TO RELATED APPLICATION

This application is the U.S. national stage application of International Patent Application No. PCT/EP2019/057426, filed Mar. 25, 2019.

FIELD OF THE INVENTION

The present invention relates to therapeutic strategies to induce skeletal muscle hypertrophy, prevent atrophy or treat or prevent diseases or injuries resulting in loss of skeletal muscle tissue and/or muscle weakness. It also relates to a non-therapeutic use of skeletal muscle hypertrophy inducers.

BACKGROUND OF THE INVENTION

Muscle wasting and weakness may result from a large panel of disease states and conditions including metabolic diseases, neurologic diseases, muscle diseases, acute or chronic illness (cachexia), aging, inactivity, food starvation and even poisoning. During the last 15 years, extensive research has led to a better understanding of the signalling pathways implicated in the loss of muscle mass. However, to date, the offer of therapeutic strategies directly targeting the muscle remains poor.

Muscle loss may occur, in particular, with aging and is a component of the frailty syndrome. Named "sarcopenia", this degenerative loss results in direct muscle atrophy and carries an increased risk for poor health outcomes including falls, incident disability, hospitalization, and mortality. With a growing older population, sarcopenia is an ever increasing global health concern and there has been great interest in developing approaches to counteract the effects of sarcopenia, and thereby reduce the age-related decline and disability. Potential interventions for sarcopenia may include physical activity and nutritional supplementation but, to date, pharmacological interventions have shown limited efficacy.

Muscle weakness can also directly result from neuromuscular disorders such as myopathies, neuromuscular junction diseases or motor neuron diseases.

Myopathies are neuromuscular disorders in which the primary symptom is muscle weakness due to dysfunction of skeletal muscle fibres. Myopathies can be inherited or acquired and include, for example, muscular dystrophies, metabolic myopathies such as mitochondrial myopathies or drug-induced myopathies, and autoimmune myopathies such as dermatomyositis, polymyositis or inclusion body myositis.

Among myopathies, muscular dystrophies represent a large group causing a progressive degeneration of myofibers and resulting in a loss of muscle mass. Mutations in over 30 genes causing muscular dystrophies have been identified. Duchenne Muscular Dystrophy (DMD) is the most common form of muscular dystrophy with an occurrence rate of about one in 3,500 males worldwide.

Treatments for neuromuscular disorders depend on the disease and specific causes, however, to date, there is no specific treatment to stop or reverse any form of muscular dystrophy. Exercise and nutritional interventions have merit for slowing the rate of muscle atrophy in some muscle wasting conditions, but in most cases they cannot halt the wasting process.

Therefore, there is a strong need for new therapeutic options that can efficiently attenuate muscle atrophy, promote muscle growth, increase muscle mass and ultimately improve the quality of life for patients.

SUMMARY OF THE INVENTION

The object of the present invention is to provide new therapeutic strategies to induce skeletal muscle hypertrophy, or prevent muscular atrophy, promote skeletal muscle regeneration, and treat or prevent skeletal muscle wasting.

Accordingly, the present invention relates to an ALK5 inhibitor for use in the treatment or prevention of a disease or disorder resulting in loss of skeletal muscle tissue and/or muscle weakness, optionally in combination with a glucocorticoid.

It also relates to a pharmaceutical composition comprising an ALK5 inhibitor and a glucocorticoid, and a pharmaceutical acceptable excipient, in particular for use in the treatment or prevention of a disease or disorder resulting in loss of skeletal muscle tissue and/or muscle weakness.

The invention further relates to a kit comprising an ALK5 inhibitor and a glucocorticoid as a combined preparation for simultaneous, separate or sequential use, preferably for use in the treatment of a disease or disorder resulting in loss of skeletal muscle tissue and/or muscle weakness.

The ALK5 inhibitor may be selected from the group consisting of RepSox, SB 525334, SD208, SB 505124, R268712, LY 364947, GW 788388, D 4476 and A 83-01, and any pharmaceutically acceptable salt, hydrate, solvate or prodrug thereof. Preferably, the ALK5 inhibitor is selected from the group consisting of RepSox, SB 525334, SD208, SB 505124, R268712, GW 788388, D 4476 and A 83-01, and any pharmaceutically acceptable salt, hydrate, solvate or prodrug thereof. More preferably, the ALK5 inhibitor is selected from the group consisting of RepSox, SB 505124, R268712, GW 788388, D 4476 and A 83-01, and any pharmaceutically acceptable salt, hydrate, solvate or prodrug thereof. Even more preferably, the ALK5 inhibitor is selected from the group consisting of RepSox and GW 788388, and any pharmaceutically acceptable salt, hydrate, solvate or prodrug thereof. Even more preferably, the ALK5 inhibitor is RepSox, or any pharmaceutically acceptable salt, hydrate, solvate or prodrug thereof.

The glucocorticoid may be selected from the group consisting of prednisolone, prednisone, cortisone, corticosterone, hydrocortisone, fludrocortisone, fluorometholone, deoxycorticosterone, ketoconazole, budesonide, methylprednisolone, fluticasone, clobetasol, clobetasone, fluocinolone, flunisolide, mometasone, prednicarbate, amcinonide, diflucortolone, beclomethasone, betamethasone, dexamethasone, triamcinolone and deflazacort, and any pharmaceutically acceptable salt, hydrate, solvate or prodrug thereof, preferably from the group consisting of prednisolone, prednisone and deflazacort, and any pharmaceutically acceptable salt, hydrate, solvate or prodrug thereof. Preferably, the glucocorticoid is selected from the group consisting of prednisolone, prednisone, cortisone, corticosterone, fludrocortisone, fluorometholone, deoxycorticosterone, ketoconazole, budesonide, methylprednisolone, fluticasone, clobetasol, clobetasone, fluocinolone, flunisolide, mometasone, prednicarbate, amcinonide, diflucortolone, beclomethasone, betamethasone, triamcinolone and deflazacort, and any pharmaceutically acceptable salt, hydrate, solvate or prodrug thereof. More preferably, the glucocorticoid is prednisolone or prednisone, or any pharmaceutically acceptable salt, hydrate, solvate or prodrug thereof. Even more preferably, the glucocorticoid is prednisolone, or any pharmaceutically acceptable salt, hydrate, solvate or prodrug thereof.

Preferably, the ALK5 inhibitor, the pharmaceutical composition or the kit of the invention is not to be used in combination with an oxytocin receptor agonist.

The disease or disorder resulting in loss of skeletal muscle tissue and/or muscle weakness may be selected from sarcopenia, cachexia, neuromuscular diseases, muscle disuse atrophy, atrophy induced by anorexia food starvation, and muscle injuries including acute muscular injury or muscle overuse injury, preferably selected from cachexia, neuromuscular diseases, muscle disuse atrophy, atrophy induced by anorexia food starvation, and muscle injuries including acute muscular injury or muscle overuse injury. Preferably, the disease or disorder resulting in loss of skeletal muscle tissue and/or muscle weakness is a muscular dystrophy. More preferably, the disease or disorder resulting in loss of skeletal muscle tissue and/or muscle weakness is a muscular dystrophy selected from the group consisting of Duchenne muscular dystrophy, Becker muscular dystrophy, myotonic muscular dystrophies, distal muscular dystrophies such as Miyoshi muscular dystrophy, and limb-girdle muscular dystrophies. Even more preferably, the disease or disorder resulting in loss of skeletal muscle tissue and/or muscle weakness is Duchenne muscular dystrophy.

The disease or disorder resulting in loss of skeletal muscle tissue and/or muscle weakness may also be a motor neuron disease, preferably selected from the group consisting of amyotrophic lateral sclerosis, primary lateral sclerosis, progressive muscular atrophy, progressive bulbar palsy, pseudobulbar palsy and spinal muscular atrophies, more preferably is a spinal muscular atrophy.

Alternatively, the disease or disorder resulting in loss of skeletal muscle tissue and/or muscle weakness may be a neuromuscular junction disease, preferably selected from the group consisting of myasthenia gravis, autoimmune neuromyotonia (Isaacs' syndrome), Lambert-Eaton myasthenic syndrome, and a neuromuscular junction disease resulted from a form of poison that effects neuromuscular junction functioning such as snake venom or neurotoxins.

The ALK5 inhibitor, the pharmaceutical composition or the kit of the invention may be used in combination with another active ingredient, preferably an active ingredient selected from the group consisting of anti-inflammatories, protein anabolic agents, antineoplastic agents, antibiotics, local anesthetics, anabolic/androgenic steroids, glucocorticoids, appetite stimulants, cytokine modulators, angiotensin and beta-adrenoreceptor inhibitors, NHE-1 inhibitors, anti-fibrotic drugs, phosphodiesterase 5 (PDE5) inhibitors, dehydroepiandrosterone, Vitamin D, ursolic acid, omega 3 acids, angiotensin-converting enzyme (ACE) inhibitors, proteasome inhibitors, cyclophilin D inhibitors, PGC-1a (alpha) pathway modulators, myostatin and activin A antagonists, ghrelin agonists, β2-adrenoreceptor agonists, creatine supplements, antifibrotic drugs, muscle ischemia therapies, mutation specific therapies, agents for therapeutic nonsense suppression, utrophin upregulators, gene replacement therapies or cell therapies using muscle precursor cells or stem cells. More preferably, said another active ingredient is a gene replacement therapy.

DETAILED DESCRIPTION OF THE INVENTION

Figure 1:
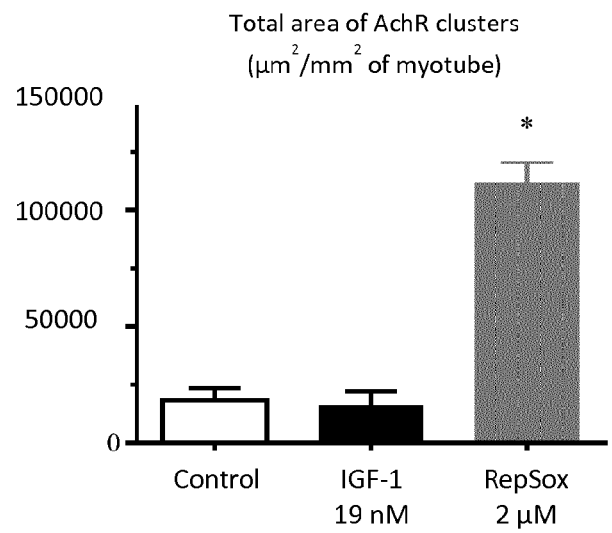
FIG. 1: RepSox activity on AchR clustering. Effect of IGF-1 and RepSox on AChR clusters in myotubes differentiated for 8 days. n=3-6 wells; *p≤0.05 versus control myotubes by Mann-Whitney analysis.

Activin receptor-like kinase 5 (ALK-5) is also known as transforming growth factor beta receptor 1 (Gene ID: 7046). This protein is a serine/threonine protein kinase which forms a heteromeric complex with type II TGF-beta receptors when bound to TGF-beta, transducing the TGF-beta signal from the cell surface to the cytoplasm. This protein is involved in the regulation of a plethora of physiological and pathological processes including cell cycle arrest in epithelial and hematopoietic cells, control of mesenchymal cell proliferation and differentiation, wound healing, extracellular matrix production, immunosuppression and carcinogenesis.

Thanks to their solid knowledge on micropattern technology and a proprietary physiological human skeletal muscle model (MyoScreen™, CYTOO) allowing fully maturation of human primary myoblasts and providing myotubes with a high level of striation, high fusion index with aligned nuclei and low morphological variability, the inventors herein surprisingly demonstrated that ALK5 inhibitors are able to induce skeletal muscle hypertrophy not only on myotubes from healthy donors but also on myotubes from DMD subjects. They showed that ALK5 inhibitors are not only able to increase myotube differentiation and size and to provide myotubes with strong contractile activity, but are also able to prevent muscular atrophy. They further demonstrated that the combination of ALK5 inhibitors and glucocorticoids provides a synergetic effect on myotube differentiation and size.

Accordingly, in a first aspect, the present invention relates to an ALK5 inhibitor for use as skeletal muscle hypertrophy inducers, to promote skeletal muscle regeneration, to prevent skeletal muscle atrophy, or in the treatment or prevention of a disease or injury resulting in loss of skeletal muscle tissue and/or muscle weakness.

The present invention thus relates to an ALK5 inhibitor for use as skeletal muscle hypertrophy inducer.

As used herein, the term "ALK5 inhibitor" refers to a molecule which inhibits or reduces the activity of ALK5, i.e. which inhibits or reduces the transduction of the TGF-beta signal from the cell surface to the cytoplasm. In particular, the ALK5 inhibitor may act through the inhibition or reduction of TGF-β binding, through the inhibition or reduction of the expression of ALK5, or through the inhibition or reduction of ALK5 kinase activity. An ALK5 inhibitor inducing an inhibition or reduction of TGF-β binding may bind TGF-β and/or ALK5 in order to prevent the interaction between the ligand and the receptor. The capacity of a compound to inhibit ALK5 may be assessed by any method known by the skilled person such as ALK5 binding assays, TGF-β cellular assays or ALK5 kinase assays as described in the articles of De Gouville et al. (Br J Pharmacol. 2005 May; 145(2):166-77), Huynh et al. (Journal of biomolecular screening 16(7); 2011) or Ma et al. (Expert Opin Drug Discov. 2008 June; 3(6): 607-621).

The ALK5 inhibitor may covalently or non-covalently bind to ALK5 and thus modify its activity by steric hindrance or modification. This inhibitor can be, for instance, a small molecule, a substrate-like peptide inhibitor (i.e. a bait-substrate), an aptamer or an antibody directed against ALK5. The inhibition can also be due to a reduction or suppression of the TGFBR1 gene expression, for example by using specific RNAi, antisense, ribozyme, or knockout or gene editing tools such as CRISPR/Cas9, TALEN, or Zinc finger nuclease.

Alternatively, the ALK5 inhibitor may covalently or non-covalently bind to TGF-β and thus prevent its interaction with ALK5. This inhibitor can be, for instance, a dominant-negative mutants of ALK5, i.e. a mutated form of ALK5 which is able to bind to TGF-β but is unable to transduce to signal, or an aptamer or an antibody directed against TGF-β. Examples of such dominant dominant-negative mutants of ALK5 include, but are not limited to, those described in Schniewind et al. (Oncogene. 2007 Jul. 19; 26(33):4850-62), and monoclonal antibodies LY2382770 and fresolimumab directed against TGF-β.

Preferably, the ALK5 inhibitor is selected from the group consisting of small molecules, nucleic acid molecules interfering specifically with ALK5 expression, bait-substrates, dominant-negative mutants of ALK5, and aptamers or antibodies directed against ALK5. More preferably, the ALK5 inhibitor is selected from the group consisting of small molecules, preferably small molecules inhibiting TGF-β binding or ALK5 kinase activity, nucleic acid molecules interfering specifically with ALK5 expression and bait-substrates. Even more preferably, the ALK5 inhibitor is selected from the group consisting of small molecules and nucleic acid molecules interfering specifically with ALK5 expression. In most preferred embodiments, the ALK5 inhibitor is a small molecule, preferably a small molecule inhibiting TGF-β binding or ALK5 kinase activity, more preferably a small molecule inhibiting ALK5 kinase activity.

In an embodiment, the ALK5 inhibitor is a nucleic acid molecule interfering specifically with ALK5 expression. As used herein, the term "nucleic acid molecule" includes, but is not limited to, RNAi, antisense and ribozyme molecules. In the present invention, a "nucleic acid molecule interfering specifically with ALK5 expression" is a nucleic acid molecule which is able to reduce or to suppress the expression of the TGFBR1 gene, in a specific way. As used herein, the term "RNAi" refers to any RNA which is capable of down-regulating the expression of the targeted protein. It encompasses small interfering RNA (siRNA), double-stranded RNA (dsRNA), single-stranded RNA (ssRNA), micro-RNA (miRNA), and short hairpin RNA (shRNA) molecules. Methods of designing, producing and using such interfering nucleic acid molecule are well known by the skilled person. Examples of such interfering nucleic acid molecules include, but are not limited to, siRNAs targeting TGFBR1 described in Wang et al. (J Invest Dermatol. 2014 July; 134(7):2016-2025), Cheng et al. (Mol Pharm. 2009; 6(3): 772-779) or Curado et al. (Mol Cell Biol. 2014 December; 34(24):4389-403).

In another embodiment, the ALK5 inhibitor is a bait-substrate. As used herein, the term "bait-substrate" designates a substrate-like peptide inhibitor, i.e. a peptide which is able to bind to ALK5 and thus prevent interaction of ALK5 with its substrate, in particular with TGF-β. Examples of such bait-substrates include, but are not limited to, TGF-β latency-associated peptide (LAP) which forms a complex with TGF-β and prevents its interaction with ALK5 (Bottinger et al. Proc Natl Acad Sci USA. 1996 Jun. 11; 93(12):5877-82).

In another embodiment, the ALK5 inhibitor is an antibody directed against ALK5 or directed against TGF-β, preferably an antibody directed against ALK5. The term "antibody" herein is used in the broadest sense and specifically covers monoclonal antibodies, polyclonal antibodies, antibody fragments, and derivatives thereof, so long as they specifically bind to the molecular target of interest. As used herein, the term "antibody fragment" refers to a protein comprising a portion of a full length antibody, generally the antigen binding or variable domain thereof. Examples of antibody fragments include Fab, Fab', F(ab)$_2$, F(ab')$_2$, F(ab)$_3$, Fv (typically the VL and VH domains of a single arm of an antibody), single-chain Fv (ScFv), dsFv, Fd (typically the VH and CH1 domains) and dAb (typically a VH domain) fragments, nanobodies, minibodies, diabodies, triabodies, tetrabodies, kappa bodies, linear antibodies, and other antibody fragments that retain antigen-binding function (e.g. Holliger and Hudson, Nat Biotechnol. 2005 September; 23(9):1126-36). Antibody fragments can be made by various techniques, including but not limited to proteolytic digestion of intact antibody as well as recombinant host cells (e.g. *E. coli* or phage). These techniques are well-known by the skilled person and are extensively described in the literature. The term "antibody derivative", as used herein, refers to an antibody provided herein, e.g. a full-length antibody or a fragment of an antibody, wherein one or more of the amino acids are chemically modified, e.g. by alkylation, PEGylation, acylation, ester or amide formation or the like.

In another embodiment, the ALK5 inhibitor is an aptamer directed against ALK5. The aptamer may be a peptide aptamer or a nucleic acid aptamer. Peptides aptamers consist of a short variable peptide loop attached at both ends to a protein scaffold such as the bacterial protein thioredoxin-A. Typically, the variable loop length is composed of ten to twenty amino acids. Peptide aptamer specific of a target of interest may be selected using any method known by the skilled person such as the yeast two-hybrid system or Phage Display. Peptides aptamers may be produced by any method known by the skilled person such as chemical synthesis or production in a recombinant bacterium followed by purification. Nucleic acid aptamers are a class of small nucleic acid ligands that are composed of RNA or single-stranded DNA oligonucleotides and have high specificity and affinity for their targets. Systematic Evolution of Ligands by EXponential enrichment (SELEX) technology to develop nucleic acid aptamers specific of a target of interest, is well known by the skilled person and may be used to obtain aptamers specific of a particular molecular target. Nucleic acid aptamers may be produced by any method known by the skilled person such as chemical synthesis or in vitro transcription for RNA aptamers. Nucleic acid aptamers may be selected from the group consisting of DNA aptamers, RNA aptamers, XNA aptamers (nucleic acid aptamer comprising xeno nucleotides) and spiegelmers (which are composed entirely of an unnatural L-ribonucleic acid backbone). Examples of such anti-ALK5 aptamers include, but are not limited to, peptide aptamers which bind to the extracellular domain of ALK5 as described in Li et al. Mol Biosyst. 2010 December; 6(12):2392-402.

In a preferred embodiment, the ALK5 inhibitor is a small molecule inhibiting ALK5 activity, preferably a small molecule inhibiting or reducing TGF-β binding to ALK5 or ALK5 kinase activity, more preferably a small molecule inhibiting or reducing ALK5 kinase activity.

As used herein, the term "small molecule" refers to small molecule that can be an organic or inorganic compound, usually less than 1000 daltons. This small molecule can be derived from any known organism (including, but not limited to, animals, plants, bacteria, fungi and viruses) or can be a synthetic molecule.

The small molecule may be selected from the group consisting of

RepSox
(CAS number: 446859-33-2)

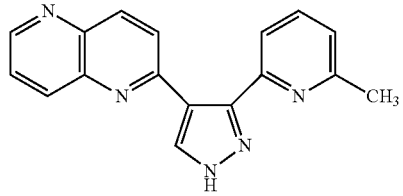 [SMILES: Cc1cccc(-c2n[nH]cc2-c2ccc3ncccc3n2)n1]

SB 525334
(CAS number: 356559-20-1)

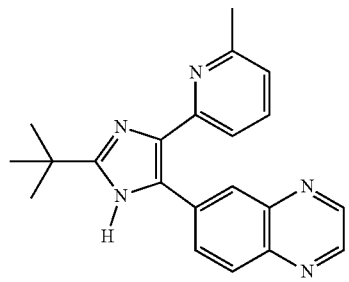 [SMILES: Cc1cccc(-c2nc(C(C)(C)C)[nH]c2-c2ccc3nccnc3c2)n1]

SD208
(CAS number: 627536-09-8)

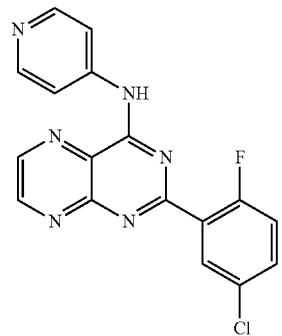 [SMILES: Fc1ccc(Cl)cc1-c1nc(Nc2ccncc2)c2nccnc2n1]

SB 505124
(CAS number: 694433-59-5)

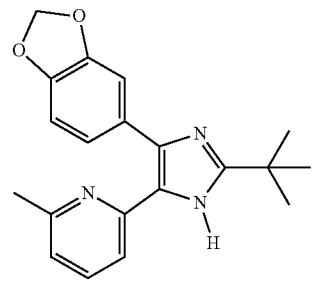 [SMILES: Cc1cccc(-c2[nH]c(C(C)(C)C)nc2-c2ccc3c(c2)OCO3)n1]

-continued
R268712
(CAS number: 879487-87-3)
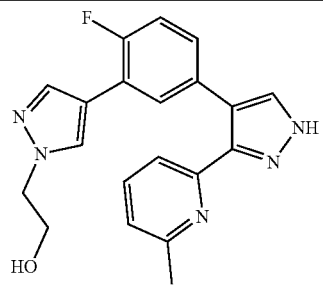
LY 364947
(CAS number: 396129-53-6)
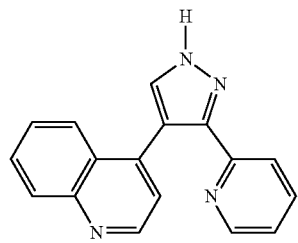 [SMILES: c1ccc(-c2n[nH]cc2-c2ccnc3ccccc23)nc1]
GW 788388
(CAS number: 452342-67-5)
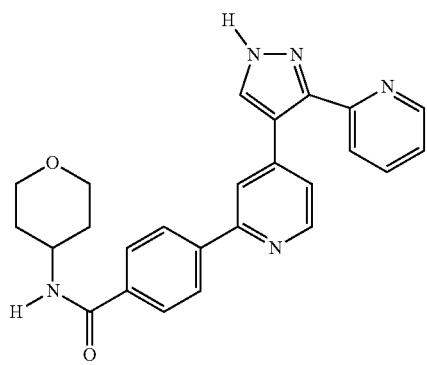 [SMILES: O=C(NC1CCOCC1)c1ccc(-c2cc(-c3c[nH]nc3-c3ccccn3)ccn2)cc1]
D 4476
(CAS number: 301836-43-1)
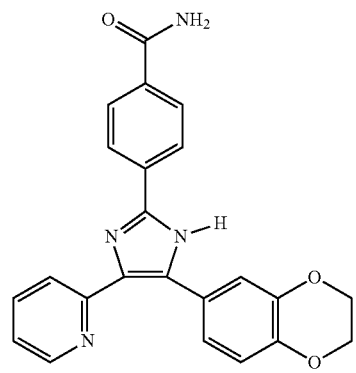 [SMILES: NC(=O)c1ccc(-c2nc(-c3ccccn3)c(-c3ccc4c(c3)OCCO4)[nH]2)cc1]
A 83-01
(CAS number: 909910-43-6)
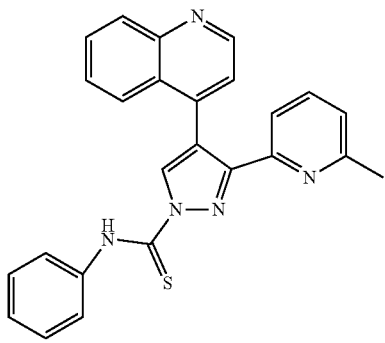 [SMILES: Cc1cccc(-c2nn(C(=S)Nc3ccccc3)cc2-c2ccnc3ccccc23)n1]

and any pharmaceutically acceptable salt, hydrate, solvate or prodrug thereof.

Preferably, the small molecule is selected from the group consisting of RepSox, SB 525334, SD208, SB 505124, R268712, GW 788388, D 4476 and A 83-01, and any pharmaceutically acceptable salt, hydrate, solvate or prodrug thereof.

More preferably, the small molecule is selected from the group consisting of RepSox, SB 505124, R268712, GW 788388, D 4476 and A 83-01, and any pharmaceutically acceptable salt, hydrate, solvate or prodrug thereof. Even more preferably, the small molecule is selected from the group consisting of RepSox and GW 788388, and any pharmaceutically acceptable salt, hydrate, solvate or prodrug thereof.

In the most preferred embodiments, the small molecule is RepSox, or any pharmaceutically acceptable salt, hydrate, solvate or prodrug thereof.

The inventors demonstrated herein that the combination of ALK5 inhibitors and glucocorticoids provides a synergetic effect on myotube differentiation and size.

Accordingly, in all aspects of the present invention (uses, methods, compositions, etc.), the ALK5 inhibitor may be used in combination with one or several glucocorticoids. In particular, the ALK5 inhibitor may be used as skeletal muscle hypertrophy inducer(s), to promote skeletal muscle regeneration, to prevent skeletal muscle atrophy, or in the treatment or prevention of a disease or injury resulting in loss of skeletal muscle tissue and/or muscle weakness, in combination with one or several glucocorticoids.

The present invention thus relates to an ALK5 inhibitor for use as skeletal muscle hypertrophy inducer, in combination with one or several glucocorticoids.

Glucocorticoids, or glucocorticosteroids, are corticosteroids that bind to the glucocorticoid receptor. They affect cells by binding to said glucocorticoid receptor and are distinguished from mineralocorticoids and sex steroids by this specific receptor. The glucocorticoid may be any glucocorticoid known by the skilled person, preferably a synthetic glucocorticoid.

Preferably, the glucocorticoid is selected from the group consisting of prednisolone, prednisone, cortisone, corticosterone, hydrocortisone, fludrocortisone, fluorometholone, deoxycorticosterone, ketoconazole, budesonide, methylprednisolone, fluticasone, clobetasol, clobetasone, fluocinolone, flunisolide, mometasone, prednicarbate, amcinonide, diflucortolone, beclomethasone, betamethasone, dexamethasone, triamcinolone and deflazacort, and any pharmaceutically acceptable salt, hydrate, solvate or prodrug thereof.

More preferably, the glucocorticoid is selected from the group consisting of prednisolone, prednisone, cortisone, corticosterone, fludrocortisone, fluorometholone, deoxycorticosterone, ketoconazole, budesonide, methylprednisolone, fluticasone, clobetasol, clobetasone, fluocinolone, flunisolide, mometasone, prednicarbate, amcinonide, diflucortolone, beclomethasone, betamethasone, triamcinolone and deflazacort, and any pharmaceutically acceptable salt, hydrate, solvate or prodrug thereof.

Even more preferably, the glucocorticoid is selected from the group consisting of prednisolone prednisone and deflazacort, and any pharmaceutically acceptable salt, hydrate, solvate or prodrug thereof.

In the most preferred embodiments, the glucocorticoid is prednisolone or prednisone, or any pharmaceutically acceptable salt, hydrate, solvate or prodrug thereof.

ALK5 inhibitor(s) and glucocorticoid(s) may be used formulated in a single pharmaceutical composition or in separate pharmaceutical compositions.

They can be administered simultaneously, sequentially or separately. As used herein, the term "simultaneously" refers to an administration of the compounds with less than 10 min between the administration of the first compound and the administration of the other(s). As used herein, the term "sequentially" refers to an administration of the compounds with less than 1 hour between the administration of the first compound and the administration of the other(s). As used herein, the term "separately" refers to an administration of the compounds with one hour or more between the administration of the first compound and the administration of the other(s).

In some preferred embodiments, the ALK5 inhibitor is selected from the group consisting of RepSox and GW 788388, and any pharmaceutically acceptable salt, hydrate, solvate or prodrug thereof, and is used in combination with a glucocorticoid is selected from the group consisting of prednisolone, prednisone and deflazacort, and any pharmaceutically acceptable salt, hydrate, solvate or prodrug thereof. In some other preferred embodiments, the ALK5 inhibitor is selected from the group consisting of RepSox and GW 788388, and any pharmaceutically acceptable salt, hydrate, solvate or prodrug thereof, and is used in combination with a glucocorticoid is selected from the group consisting of prednisolone and prednisone, and any pharmaceutically acceptable salt, hydrate, solvate or prodrug thereof. In some other preferred embodiments, the ALK5 inhibitor is selected from the group consisting of RepSox and any pharmaceutically acceptable salt, hydrate, solvate or prodrug thereof, and is used in combination with a glucocorticoid is selected from the group consisting of prednisolone and prednisone, and any pharmaceutically acceptable salt, hydrate, solvate or prodrug thereof.

The ALK5 inhibitors and glucocorticoids may be used in the form of pharmaceutically acceptable salts, hydrates, solvates or prodrug, preferably in the form of pharmaceutically acceptable salts, hydrates, solvates, more preferably in the form of pharmaceutically acceptable salts. In preferred embodiments, all ALK5 inhibitors and glucocorticoids are used in the form of pharmaceutically acceptable salts, hydrates or solvates, more preferably in the form of pharmaceutically acceptable salts.

Said pharmaceutically acceptable salts, hydrates and solvates may be formed, where appropriate, by methods well known to those of skill in the art.

The term "pharmaceutically acceptable salt" refers to salts which are non-toxic for a patient and suitable for maintaining the stability of a therapeutic agent and allowing the delivery of said agent to target cells or tissue. Pharmaceutically acceptable salts are well known in the art.

As used herein, the term "solvate" refers to a solvent addition form that contains either stoichiometric or non stoichiometric amounts of solvent. Some compounds have a tendency to trap a fixed molar ratio of solvent molecules in the crystalline solid state, thus forming a solvate. If the solvent is water, the solvate formed is a hydrate. When the solvent is alcohol, the solvate formed is an alcoholate. Hydrates are formed by the combination of one or more molecules of water with one of the substances in which the water retains its molecular state as $H_2O$, such combination being able to form one or more hydrates.

The ALK5 inhibitors and glucocorticoids may also be used in the form of a prodrug. Prodrugs are generally drug precursors that, following administration to an individual and subsequent absorption, are converted to an active, or a more active species via some process, such as conversion by a metabolic pathway. Some prodrugs have a chemical group present on the prodrug that, for example, renders it less active, increases its solubility and/or improves safety profiles over administration of the parent drugs. In some instances, the prodrugs may be less susceptible to in vivo degradation and exhibit a greater half-life than its parent drug. Once the chemical group has been cleaved and/or modified from the prodrug, the active drug is generated. Prodrugs are often useful because, in some situations, they are easier to administer than the parent drug. They are, for instance, bioavailable by oral administration whereas the parent is not. In certain instances, the prodrug also has improved solubility in pharmaceutical compositions over the parent drug. An example, without limitation, of a prodrug would be a compound as described herein which is administered and subsequently subjected to a biotransformation in vivo and thus provides a therapeutically effective concentration of an active agent. For further general examples, see: Bundgaard, "Design and Application of Prodrugs" in A Textbook of Drug Design and Development, Krosgaard-Larsen and Bundgaard, Ed., 1991, Chapter 5, 113-191, which is incorporated herein by reference. Prodrugs may be prepared, for example, by modifying functional groups present in the compound in such a way that the modifications are cleaved, either in routine manipulation or in vivo, to the parent compound.

The present invention also relates to a pharmaceutical composition comprising an ALK5 inhibitor and a pharmaceutically acceptable excipient, preferably for use as skeletal muscle hypertrophy inducer.

All embodiments described above for the ALK5 inhibitors as skeletal muscle hypertrophy inducers are also encompassed in this aspect.

The pharmaceutical composition of the invention is formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

Possible pharmaceutical compositions include those suitable for oral, transmucosal (including nasal, rectal or vaginal), topical (including transdermal, buccal and sublingual), or parenteral (including subcutaneous, intramuscular, intravenous and intradermal) administration. For these formulations, conventional excipient can be used according to techniques well known by those skilled in the art. Preferably, the pharmaceutical composition of the invention is suitable for oral administration.

The compositions for parenteral administration are generally physiologically compatible sterile solutions or suspensions which can optionally be prepared immediately before use from solid or lyophilized form. Adjuvants such as a local anesthetic, preservative and buffering agents can be dissolved in the vehicle and a surfactant or wetting agent can be included in the composition to facilitate uniform distribution of the active ingredient.

For oral administration, the composition can be formulated into conventional oral dosage forms such as tablets, capsules, powders, granules and liquid preparations such as syrups, elixirs, and concentrated drops. Non toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical composition according to the invention may be formulated to release the active drug substantially immediately upon administration or at any predetermined time or time period after administration.

Pharmaceutical composition according to the invention can comprise one or more ALK5 inhibitors associated with one or several pharmaceutically acceptable excipients. These excipients are chosen according to the form of administration as described above.

Pharmaceutical composition according to the invention may also comprise one or several additional active compounds. Said additional active compounds may be selected, for example, from the group consisting of anti-inflammatoires, protein anabolic agents (e.g. growth hormone or insulin-like growth factor I), antineoplastic agents, antibiotics, local anesthetics, anabolic/androgenic steroids (e.g. testosterone), glucocorticoids, appetite stimulants (e.g. dronabinol), cytokine modulators (e.g. thalidomide), angiotensin and beta-adrenoreceptor inhibitors, NHE-1 inhibitors (e.g. rimeporide), antifibrotic drugs (e.g. losartan or Lisinopril), phosphodiesterase 5 (PDE5) inhibitors (e.g. tadalafil or sildenafil), dehydroepiandrosterone, Vitamin D, ursolic acid, omega 3 acids, angiotensin-converting enzyme (ACE) inhibitors, proteasome inhibitors, cyclophilin D inhibitors, PGC-1 a (alpha) pathway modulators, myostatin and activin A antagonists, ghrelin agonists, β2-adrenoreceptor agonists, creatine supplements, antifibrotic drugs such as losartan and lisinopril, muscle ischemia therapies such as tadalafil and sildenafil, mutation specific therapies such as exon skipping therapies (e.g. eteplirsen, a morpholino phosphorodiamidate antisense oligomer targeting mutations implicated in DMD cases), and agents for therapeutic nonsense suppression such as ataluren, utrophin upregulators such as SMT-C1100.

As described above, the pharmaceutical composition of the invention may comprise, or may be used in combination with, one or several glucocorticoids.

In a particular embodiment, the pharmaceutical composition according to the invention comprises one or several ALK inhibitors and one or several glucocorticoids, preferably one ALK inhibitor and one glucocorticoid.

The present invention also relates to a kit comprising an ALK5 inhibitor and a glucocorticoid as a combined preparation for simultaneous, separate or sequential use, preferably for use as skeletal muscle hypertrophy inducer. In particular, the kit may comprise a pharmaceutical composition comprising an ALK5 inhibitor and a pharmaceutically acceptable excipient and another pharmaceutical composition comprising a glucocorticoid and a pharmaceutically acceptable excipient.

Preferably, the pharmaceutical composition or the kit comprises an ALK5 inhibitor selected from the group consisting of RepSox, SB 525334, SD208, SB 505124, R268712, LY 364947, GW 788388, D 4476 and A 83-01, and any pharmaceutically acceptable salt, hydrate, solvate or prodrug thereof, and a glucocorticoid selected from the group consisting of prednisolone, prednisone, cortisone, corticosterone, hydrocortisone, fludrocortisone, fluorometholone, deoxycorticosterone, ketoconazole, budesonide, methylprednisolone, fluticasone, clobetasol, clobetasone, fluocinolone, flunisolide, mometasone, prednicarbate, amcinonide, diflucortolone, beclomethasone, betamethasone, dexamethasone, triamcinolone and deflazacort, and any pharmaceutically acceptable salt, hydrate, solvate or prodrug thereof.

More preferably, the pharmaceutical composition or the kit comprises an ALK5 inhibitor selected from the group consisting of RepSox and GW 788388, and any pharmaceutically acceptable salt, hydrate, solvate or prodrug thereof, and a glucocorticoid selected from the group consisting of prednisolone, prednisone and deflazacort, and any pharmaceutically acceptable salt, hydrate, solvate or prodrug thereof, preferably selected from the group consisting of prednisolone and prednisone, and any pharmaceutically acceptable salt, hydrate, solvate or prodrug thereof.

Even more preferably, the pharmaceutical composition or the kit comprises an ALK5 inhibitor selected from the group consisting of RepSox and any pharmaceutically acceptable salt, hydrate, solvate or prodrug thereof, and a glucocorticoid selected from the group consisting of prednisolone and prednisone, and any pharmaceutically acceptable salt, hydrate, solvate or prodrug thereof.

In the experimental section, the inventors demonstrated that ALK5 inhibitors are able to promote the differentiation of myoblasts into myotubes, to increase the number and size of myotubes, and/or to increase the fusion index reflecting the capacity of cells to regenerate.

Accordingly, the present invention relates to an ALK5 inhibitor, a pharmaceutical composition or kit according to the invention, for use as skeletal muscle hypertrophy inducer.

Skeletal muscle fibers are syncytia that arise from the sequential fusion of myoblast cells. The process involves i) the differentiation of myoblasts into myocytes, ii) the fusion of myocytes to form nascent myotubes and iii) additional fusion of myocytes with nascent myotubes to form more mature myotubes. Accordingly, as used herein, the expression «skeletal muscle hypertrophy»refers to a gain of skeletal muscle mass characterized by an increase in the size of pre-existing myofibers and/or an increase in the number of myofibers and/or an increase in the mean number of nuclei per myotube and/or an increase in the fusion index (number of nuclei in myotubes divided by total number of nuclei in myoblasts and myotubes). Preferably, the expression «skeletal muscle hypertrophy»refers by an increase in the size of pre-existing myofibers and/or an increase in the number of myofibers and/or an increase in the fusion index. As used herein, the terms "myotube" and "myofiber" are used interchangeably.

The present invention also relates to a method for inducing skeletal muscle hypertrophy in a subject in need thereof, comprising administering a therapeutically effective amount of an ALK5 inhibitor or a pharmaceutical composition according to the invention, to said subject.

The therapeutically effective amount to be administered may be easily chosen by the skilled person and should be sufficient to provide an increase of skeletal muscle mass or skeletal muscle strength in the subject.

As used herein, the subject is an animal, preferably a mammal, more preferably a human being. Preferably, the subject is a subject suffering from muscle wasting or weakness resulting from a disease or disorder resulting in loss of skeletal muscle tissue and/or skeletal muscle weakness, such as diseases or disorders described below.

The present invention further concerns the use of an ALK5 inhibitor or a pharmaceutical composition according to the invention for preparing a medicament inducing skeletal muscle hypertrophy, optionally said medicament being intended to be used in combination with one or several glucocorticoids.

As described above, the ALK5 inhibitor or the pharmaceutical composition of the invention may be used in combination with, one or several glucocorticoids.

The present invention also relates to an ALK5 inhibitor or a pharmaceutical composition or kit according to the invention, for use to prevent involuntary loss of skeletal muscle mass, preferably due to the degeneration of muscle fibers, for use to promote or stimulate skeletal muscle mass increase, for use to replete skeletal muscle mass and/or for use to increase skeletal muscle mass and/or strength.

The present invention also relates to a method for preventing involuntary loss of skeletal muscle mass, preferably due to the degeneration of muscle fibers, promoting or stimulating skeletal muscle mass increase, repleting skeletal muscle mass and/or increasing skeletal muscle mass and/or strength, in a subject in need thereof, comprising administering a therapeutically effective amount of an ALK5 inhibitor or a pharmaceutical composition according to the invention, to said subject.

The therapeutically effective amount to be administered may be easily chosen by the skilled person and should be sufficient to prevent involuntary loss of skeletal muscle mass, to promote or stimulate skeletal muscle mass increase, to replete skeletal muscle mass and/or to increase skeletal muscle mass and/or strength.

The subject may be as defined above.

The present invention further concerns the use of an ALK5 inhibitor or a pharmaceutical composition according to the invention, for preparing a medicament preventing involuntary loss of skeletal muscle mass, preferably due to the degeneration of muscle fibers, promoting or stimulating skeletal muscle mass increase, repleting skeletal muscle mass and/or increasing skeletal muscle mass and/or strength, optionally said medicament being intended to be used in combination with one or several glucocorticoids.

As described above, the ALK5 inhibitor or the pharmaceutical composition of the invention may be used in combination with, one or several glucocorticoids.

In the experimental section, the inventors demonstrated that ALK5 inhibitors are not only able to promote the differentiation of myoblasts into myotubes and to increase the fusion index reflecting the capacity of cells to regenerate, but are also able to prevent skeletal muscle atrophy, in particular atrophy induced by IL-1β, TNF-α, myostatin, TGF-β and dexamethasone.

Thus, the present invention also relates to a ALK5 inhibitor or a pharmaceutical composition or kit according to the invention, for use to promote skeletal muscle regeneration and/or prevent skeletal muscle atrophy.

All embodiments described above for the ALK5 inhibitors as skeletal muscle hypertrophy inducers are also encompassed in this aspect.

As used herein, the expression "skeletal muscle regeneration" refers to the capacity of muscle cells or tissue to regenerate, i.e. to produce new myotubes from myoblasts. The expression "to promote skeletal muscle regeneration" thus refers to the capacity of ALK5 inhibitors to promote differentiation of myoblasts into myotubes and/or to increase the number of myotubes and/or to improve the regeneration capacity of muscle tissue and in particular of myotubes.

As used herein, the expression "to prevent skeletal muscle atrophy" refers to the capacity of ALK5 inhibitors to prevent, stop or slow down muscle wasting. Muscle atrophy may be caused for example by a disease state, a particular physiological condition such as aging, food starvation or inactivity, or an atrophying agent such as drug (statins) or poison (botulinum toxin). Prevention of muscle atrophy is preferably obtained by increasing the production of muscle mass and then counter balancing muscle loss.

As described above, the ALK5 inhibitor or the pharmaceutical composition of the invention may be used in combination with, one or several glucocorticoids.

The present invention also relates to a method for promoting skeletal muscle regeneration and/or preventing skeletal muscle atrophy in a subject in need thereof, comprising administering a therapeutically effective amount of an ALK5 inhibitor or a pharmaceutical composition according to the invention, to said subject.

The therapeutically effective amount to be administered may be easily chosen by the skilled person and should be sufficient to stimulate skeletal muscle regeneration and/or prevent, stop or slow down muscle wasting, preferably by increasing the production of muscle mass and then counter balancing muscle loss.

The subject may be as defined above.

The present invention further relates to the use of an ALK5 inhibitor or a pharmaceutical composition according to the invention for preparing a medicament for promoting skeletal muscle regeneration and/or preventing skeletal muscle atrophy, optionally said medicament being intended to be used in combination with one or several glucocorticoids.

As described above, the ALK5 inhibitor or the pharmaceutical composition of the invention may be used in combination with, one or several glucocorticoids.

The present invention further relates to an ALK5 inhibitor or a pharmaceutical composition or kit according to the invention for use in the treatment or prevention of muscle wasting, and in particular in the treatment or prevention of a disease or disorder resulting in loss of skeletal muscle tissue and/or skeletal muscle weakness.

It also concerns the use of an ALK5 inhibitor or a pharmaceutical composition according to the invention for preparing a medicament for treating muscle wasting, and in particular a disease or disorder resulting in loss of skeletal muscle tissue and/or skeletal muscle weakness, optionally said medicament being intended to be used in combination with one or several glucocorticoids.

It finally concerns a method for treating muscle wasting, and in particular a disease or disorder resulting in loss of skeletal muscle tissue and/or skeletal muscle weakness, in a subject in need thereof, comprising administering a therapeutically active amount of an ALK5 inhibitor or a pharmaceutical composition according to the invention to the subject.

All embodiments described above for the ALK5 inhibitors as skeletal muscle hypertrophy inducers are also encompassed in this aspect.

As described above, the ALK5 inhibitor or the pharmaceutical composition of the invention may be used in combination with, one or several glucocorticoids.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease.

As used herein, the term "treatment of muscle wasting" may refer to the therapy, prevention or retardation of involuntary loss of skeletal muscle mass, preferably due to the degeneration of muscle fibers.

In particular, the term "treatment of a disease or disorder resulting in loss of skeletal muscle tissue and/or skeletal muscle weakness" may refer to a preservation or increase of the skeletal muscle mass and/or the skeletal muscle strength of a patient or a slow-down of the skeletal muscle mass loss and/or the skeletal muscle strength loss of a patient.

The effective amount may be a therapeutically or prophylactically effective amount. A "therapeutically effective amount" refers to an amount effective, at dosages and for periods of time necessary, to achieve the desired therapeutic or prophylactic result. The therapeutically effective amount may vary according to factors such as the disease or disorder, disease state, age, sex, and weight of the individual. A therapeutically effective amount encompasses an amount in which any toxic or detrimental effects are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

The disease or disorder to be treated may be any disease or disorder resulting in loss of skeletal muscle tissue or mass and/or skeletal muscle weakness.

Muscle wasting (i.e. loss of skeletal muscle tissue) and weakness may result from a large panel of diseases or disorders such as metabolic diseases (e.g. glycogen storage diseases, lipid storage diseases or disorders of purine nucleotide metabolism), neurologic diseases (e.g. Hereditary Sensory and Motor Neuropathies type III) and neuromuscular diseases, cachexia (i.e. muscle atrophy resulting from diseases such as cancer, AIDS, congestive heart failure, chronic obstructive pulmonary disease, severe burns, renal failure or liver failure), sarcopenia, muscle disuse atrophy (i.e. atrophy caused by prolonged inactivity), atrophy induced by excessive food starvation such as starvation due to anorexia nervosa, or muscle injuries including acute muscular injury, muscle overuse injury, or wound war injuries.

Preferably, the disease or disorder to be treated is selected from neuromuscular diseases, cachexia, sarcopenia, muscle disuse atrophy, atrophy induced by anorexia food starvation, and muscle injuries including acute muscular injury or muscle overuse injury. More preferably, the disease or disorder to be treated is selected from neuromuscular diseases, cachexia and sarcopenia.

In a particular embodiment, the disease or disorder is a neuromuscular disease, preferably selected from muscle diseases (i.e. myopathies), neuromuscular junction diseases or motor neuron diseases.

Myopathies are neuromuscular disorders in which the primary symptom is muscle weakness due to dysfunction of skeletal muscle fibres. Myopathies can be inherited or acquired and include, for example, muscular dystrophies, metabolic myopathies such as mitochondrial myopathies or drug-induced myopathies, and autoimmune myopathies such as dermatomyositis, polymyositis or inclusion body myositis.

Muscular dystrophies represent a large group of myopathies causing a progressive degeneration of myofibers and resulting in a loss of muscle mass. Mutations in over 30 genes causing muscular dystrophies have been identified. Examples of muscular dystrophies include, but are not limited to Duchenne muscular dystrophy, Becker muscular dystrophy, congenital muscular dystrophies, facioscapulohumeral muscular dystrophies, myotonic muscular dystrophies, distal muscular dystrophies such as Miyoshi muscular dystrophy, Emery-Dreifuss muscular dystrophy, limb-girdle muscular dystrophies and oculopharyngeal muscular dystrophies.

Motor neuron diseases are disorders which are characterized by the gradual degeneration and death of motor neurons which control voluntary muscles. Motor neurons thus stop sending messages to muscles which gradually weaken and atrophy. Motor neuron diseases include, for example, amyotrophic lateral sclerosis, primary lateral sclerosis, progressive muscular atrophy, progressive bulbar palsy, pseudobulbar palsy and spinal muscular atrophies.

Neuromuscular junction diseases are disorders which have in common the perturbation of the neurotransmission through the neuromuscular junction and result in progressive weakness due to a reduced muscle strength. Neuromuscular junction diseases include, for example, myasthenia gravis, autoimmune neuromyotonia (Isaacs' syndrome), Lambert-Eaton myasthenic syndrome, or may result of a form of poison that effects neuromuscular junction functioning such as snake venom or neurotoxins (e.g. *Clostridium botulinum* toxin).

Preferably, the disease or disorder is selected from muscular dystrophies, and in particular from Duchenne muscular dystrophy, Becker muscular dystrophy, myotonic muscular dystrophies, distal muscular dystrophies such as Miyoshi muscular dystrophy, and limb-girdle muscular dystrophies.

More preferably, the disease or disorder is Duchenne muscular dystrophy.

In another particular embodiment, the disease or disorder is selected from cachexia and sarcopenia, preferably is sarcopenia.

In all methods and aspects of the present invention, the ALK5 inhibitor or a pharmaceutical composition according to the invention may be used in combination with other active ingredients that can be chosen according to the desired effect or the disease to be prevented or treated. Examples of other active ingredients include, but are not limited to, anti-inflammatoires, protein anabolic agents (e.g. growth hormone or insulin-like growth factor I), antineoplastic agents, antibiotics, local anesthetics, anabolic/androgenic steroids (e.g. testosterone), glucocorticoids, appetite stimulants (e.g. dronabinol), cytokine modulators (e.g. thalidomide), angiotensin and beta-adrenoreceptor inhibitors, NHE-1 inhibitors (e.g. rimeporide), antifibrotic drugs (e.g. losartan or Lisinopril), phosphodiesterase 5 (PDE5) inhibitors (e.g. tadalafil or sildenafil), dehydroepiandrosterone, Vitamin D, ursolic acid, omega 3 acids, angiotensin-converting enzyme (ACE) inhibitors, proteasome inhibitors, cyclophilin D inhibitors, PGC-1 a (alpha) pathway modulators, myostatin and activin A antagonists, ghrelin agonists, β2-adrenoreceptor agonists, creatine supplements, antifibrotic drugs such as losartan and lisinopril, muscle ischemia therapies such as tadalafil and sildenafil, mutation specific therapies such as exon skipping therapies (e.g. eteplirsen, a morpholino phosphorodiamidate antisense oligomer targeting mutations implicated in DMD cases), agents for therapeutic nonsense suppression such as ataluren, utrophin upregulators such as SMT-C1100, gene replacement therapies (such as using rAAV2.5-CMV-Mini-dystrophy, rAAVrh74.MCK.Mini-dystrophy or rAAV1.CMV.huFollistatin344) or cell therapies using muscle precursor cells or stem cells.

Such combination therapies noted above encompass combined administration (where two or more therapeutic agents are included in the same or separate formulations), and separate administration, in which case, administration of the ALK5 inhibitor can occur prior to, simultaneously, and/or following, administration of the additional therapeutic agent.

The ALK5 inhibitor (and any additional therapeutic agent) can be administered by any suitable means, including parenteral, oral, transmucosal or topical administration, preferably oral administration.

The doses used for the administration can be adapted as a function of various parameters, and in particular as a function of the mode of administration used, of the relevant pathology, or alternatively of the desired duration of treatment. The ALK5 inhibitor (and any additional therapeutic agent) may be administered as a single dose or in multiple doses.

The amount of ALK5 inhibitor which will be effective in the treatment of a particular disorder or condition will depend on the nature of the disorder or condition, and can be determined by standard clinical techniques.

In preferred embodiments, each dose may range from about 0.0001 mg to about 300 mg per kilogram of body weight of ALK5 inhibitor, more preferably from about 0.0005 mg to about 50 mg per kilogram of body weight of ALK5 inhibitor, and even more preferably from about 0.001 mg to about 5 mg per kilogram of body weight of ALK5 inhibitor. Preferably, this dose range is a daily dose range.

In some embodiments wherein the ALK5 inhibitor is used in combination with a glucocorticoid, each dose may range from about 0.05 mg to about 100 mg per kilogram of body weight of glucocorticoid, preferably from about 0.05 mg to about 10 mg per kilogram of body weight of glucocorticoid, more preferably from about 0.1 mg to about 5 mg per kilogram of body weight of glucocorticoid, and even more preferably from about 0.1 mg to about 2 mg per kilogram of body weight of glucocorticoid. Preferably, this dose range is a daily dose range.

In a particular embodiment, the ALK5 inhibitor, preferably RepSox, is used in combination with a glucocorticoid, preferably prednisolone or prednisone, and the dose of ALK5 inhibitor is from about 0.001 mg to about 5 mg per kilogram of body weight of ALK5 inhibitor and the dose of glucocorticoid is from about 0.1 mg to about 2 mg per kilogram of body weight of glucocorticoid.

The dosing schedule for administration may vary from once a month to daily depending on a number of clinical factors, including the type of disease, severity of disease, and the subject's sensitivity to the therapeutic agent.

In some particular embodiments of all the aspects of the present invention wherein the ALK5 inhibitor is used in combination with one or several glucocorticoids (in the same or separate pharmaceutical compositions), the amounts or relative amounts of the ALK5 inhibitor(s) and of the glucocorticoid(s) are such that they exhibit a synergetic effect upon administration to a subject.

As used herein, the term "synergetic effect" means that the effect, e.g. the therapeutic effect, obtained with the combination of the ALK5 inhibitor(s) and the glucocorticoid(s) is greater than the addition of the effect of each compound used alone. In other words, the effect as skeletal muscle hypertrophy inducers, to promote skeletal muscle regeneration, to prevent skeletal muscle atrophy, or to treat or prevent a disease or injury resulting in loss of skeletal muscle tissue and/or muscle weakness, of the combination is greater than the sum of the effect of each compound alone.

The potentiating effect allows to use decreased amounts of ALK5 inhibitor and/or glucocorticoid. Thus, by combining ALK5 inhibitor(s) and glucocorticoid(s), it is possible to preserve, or even improve, the efficacy of the treatment, while reducing adverse or toxic effects.

Thus, in preferred embodiments, the ALK5 inhibitor(s) and of the glucocorticoid(s) are present in the synergetic composition or combination, or are administered to the subject in need thereof at subtherapeutic doses.

As used herein, the term "subtherapeutic dose" refers to an amount or dose of a therapeutic agent lower than the conventional dose administered to a subject for the same indication and the same administration route when it is used alone. In particular, it refers to an amount or dose of a therapeutic agent which has no or only slight effect on skeletal muscle cells when used alone.

One or several of the compounds can be administered at a therapeutic dose while the other(s) can be administered at a subtherapeutic dose. In particular, the ALK5 inhibitor(s) is(are) administered at a therapeutic dose while the glucocorticoid(s) is(are) administered at a subtherapeutic dose, or vice-versa. Preferably, in order to prevent side effects induced by the administration of glucocorticoid(s), the ALK5 inhibitor(s) is(are) administered at a therapeutic dose while the glucocorticoid(s) is(are) administered at a subtherapeutic dose from about 0.01 mg to about 0.5 mg per kilogram of body weight of glucocorticoid, preferably from about 0.1 mg to about 0.5 mg per kilogram of body weight of glucocorticoid. In a particular embodiment, the ALK5 inhibitor, preferably RepSox, is used in combination with a glucocorticoid, preferably prednisolone or prednisone, and the dose of ALK5 inhibitor is from about 0.001 mg to about 5 mg per kilogram of body weight of ALK5 inhibitor and the dose of glucocorticoid is from about 0.1 mg to about 0.5 mg per kilogram of body weight of glucocorticoid.

Alternatively, instead of lowering the amount or dosage of the compounds of the combination, the administration frequency or the treatment period may be reduced.

As shown in the experimental section, the ALK5 inhibitors are able to prevent muscle atrophy.

The present invention thus also concerns a product containing an ALK5 inhibitor as described above and a compound inducing skeletal muscular atrophy, as a combined preparation for simultaneous, separate or sequential use.

All embodiments described above for the ALK5 inhibitors as skeletal muscle hypertrophy inducers are also encompassed in this aspect.

In a particular embodiment, the compound inducing skeletal muscular atrophy is a therapeutic agent. In this embodiment, the ALK5 inhibitor is used to prevent or limit drug-induced myopathy.

The present invention further concerns a method for preventing or limiting the skeletal muscular atrophy induced by a therapeutic agent in a subject comprising administering a therapeutically effective amount of an ALK5 inhibitor as described above to said subject simultaneously, separately or sequentially to the administration of said therapeutic agent inducing skeletal muscular atrophy.

Examples of therapeutic agents inducing skeletal muscular atrophy include, but are not limited to corticosteroids, colchicine, chloroquine, hydroxychloroquine, D-penicillamine, antibiotics, betablockers, amiodarone, cimetidine, zidovudine, vincristine, clofibrate, statins, fibrates, cyclosporine, L-tryptophan, drugs causing hypokalaemia and lipid lowering agents, or combinations of drugs such as a fibrate and a statine or cyclosporin and colchicine, and therapeutic agents administered by intramuscular route such as vaccines.

In a preferred embodiment, the therapeutic agent inducing skeletal muscular atrophy include is a lipid lowering agent, preferably selected from statins and fibrates.

The ALK5 inhibitor and the therapeutic agent inducing skeletal muscular atrophy may be administered simultaneously. Alternatively, the ALK5 inhibitor may be administered to the subject prior or after administration of the therapeutic agent inducing skeletal muscular atrophy. Preferably, when the therapeutic agent and the ALK5 inhibitor are administered separately, they are both administered within 24 hours.

Optionally, as described above, the ALK5 inhibitor may be used in combination with another active ingredient, preferably in combination with one or several glucocorticoids.

ALK5 inhibitors as described above, i.e. skeletal muscle hypertrophy inducers, may also find applications in feed and food industries, in particular as dietary supplements.

Accordingly, in a further aspect, the present invention also relates to a dietary supplement composition comprising an ALK5 inhibitor, and optionally one or several glucocorticoids.

It also relates to a non-therapeutic use of an ALK5 inhibitor or a kit as defined above, or of a dietary supplement composition of the invention to increase muscle mass, muscle strength and/or muscle performance in a subject.

It further relates to a non-therapeutic use of an ALK5 inhibitor or a kit as defined above, or of a dietary supplement composition of the invention for use to prevent loss of skeletal muscle mass, preferably involuntary and/or undesired loss of skeletal muscle mass.

Optionally, as described above, the ALK5 inhibitor may be used in combination with another active ingredient, preferably in combination with one or several glucocorticoids.

The subject is preferably a mammal, more preferably a human being.

In an embodiment, the subject is a non-human animal, preferably a mammal, and even more preferably a livestock animal or a sports or leisure animal, e.g. racehorses. Livestock animals are non-human mammals, preferably mammals used for meat. In particular livestock animals may be selected from pig, cattle, goat, sheep, horse, bison, deer, elk or moose.

In another embodiment, the subject is a human being, preferably an adult human.

In a particular embodiment, the subject is an older adult human, e.g. of more than 60, and the dietary supplement composition is used, or is suitable, to stop, slow/down or prevent muscle function and/or mass decline.

The subject is preferably a healthy subject, i.e. a subject who is not suffering from a disease or disorder resulting in loss of skeletal muscle tissue and/or muscle weakness.

The dietary supplement composition may be in the form of a powder, liquid, or solid.

Preferably, the dietary supplement composition is formulated for oral administration. In particular, said dietary supplement composition may be formulated into conventional oral dosage forms such as tablets, capsules, powders, granules and liquid preparations such as syrups, elixirs, and concentrated drops. Non toxic solid carriers or diluents may be used which include, for example, mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and cross-linked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

The dietary supplement composition may comprise further ingredient providing beneficial effects to the subject such as vitamins (e.g. vitamin D), amino acids, proteins, lipids (omega 3 fatty acids), ursolic acid, tomaditine, antioxidants, polyphenols, isoflavones present in soybean and derivatives, tea leaves components and garlic compounds.

All embodiments described above for the ALK5 inhibitors and their uses, in particular, as skeletal muscle hypertrophy inducers are also encompassed in this aspect.

The present invention also relates to the use of an ALK5 inhibitor as defined above, as ingredient for animal feed composition or as additive for animal feed composition. It also relates to the use of an ALK5 inhibitor, to prepare an ingredient or additive for animal feed composition. Optionally, as described above, the ALK5 inhibitor may be used in combination with another active ingredient, preferably in combination with one or several glucocorticoids.

It further relates to an ingredient or additive for animal feed composition comprising an ALK5 inhibitor as defined above, and optionally one or several glucocorticoids.

It further relates to a feed composition for livestock comprising an ALK5 inhibitor as defined above, and optionally one or several glucocorticoids, as ingredient or additive.

The feed composition, ingredient, additive, or dietary supplement of the invention may further comprise any edible GRAS (generally recognized as safe) material such as, for example, corn gluten feed, sunflower hulls, distillers grains, guar hulls, wheat middlings, rice hulls, rice bran, oilseed meals, dried blood meal, animal by-product meal, fish by-product, fish meal, dried fish solubles, feather meal, poultry by-products, meat meal, bone meal, dried whey, soy protein concentrate, soy flour, yeast, wheat, oats, grain sorghums, corn feed meal, rye, corn, barley, aspirated grain fractions, brewers dried grains, corn flour, corn gluten meal, feeding oat meal, sorghum grain flour, wheat mill run, wheat red dog, hominy feed, wheat flour, wheat bran, wheat germ meal, oat groats, rye middlings, cotyledon fiber, ground grains, or a mixture thereof.

Preferably, the feed composition, ingredient, additive, or dietary supplement of the invention is used as non-therapeutic skeletal muscle hypertrophy inducer, and in particular to improve livestock performance, i.e. to increase liveweight gain. Thus, preferably, the feed composition, ingredient, additive, or dietary supplement is intended to be administered to a healthy subject, i.e. a subject who is not suffering from a disease or disorder resulting in loss of skeletal muscle tissue and/or muscle weakness. The subject may be as defined above for the dietary supplement composition of the invention.

The invention also relates to a method of improving livestock performance and/or health comprising providing to said livestock an ALK5 inhibitor as defined above, and optionally one or several glucocorticoids, in particular a feed composition, ingredient, additive, or dietary supplement of the invention. Preferably, as used herein, the term "improving livestock performance" refers to increase liveweight gain. This use is intended to be a non-therapeutic use as explained above and preferably, the compound, feed composition, ingredient, additive, or dietary supplement is intended to be administered to healthy livestock, i.e. who is not suffering from a disease or disorder resulting in loss of skeletal muscle tissue and/or muscle weakness.

The feed composition, ingredient, additive, or dietary supplement may be in the form of a powder, liquid, or solid.

Ingredients of the feed composition of the invention other than the ALK5 inhibitor depend on the nature of the livestock and may be easily chosen by the skilled person.

Preferably, the feed composition of the invention is in a form and/or a composition approved by a governmental institution such as National Food Administration (for example ANSES in France, ACIA in Canada, or FAD in the US).

All embodiments described above for the ALK5 inhibitors and its uses, in particular, as skeletal muscle hypertrophy inducers are also encompassed in this aspect.

Preferably, in all aspects of the present invention, the ALK5 inhibitor, optionally in combination with glucocorticoid(s), is not to be used in combination with an oxytocin receptor agonist. In particular, in preferred embodiments, the pharmaceutical composition of the invention does not comprise an oxytocin receptor agonist, and the ALK5 inhibitor, optionally in combination with glucocorticoid(s), is not to be used in combination with an oxytocin receptor agonist.

The oxytocin receptor (OXTR) is a G-protein coupled receptor for the peptide oxytocin, which acts a hormone and neurotransmitter.

An OXTR agonist is any agent that specifically enhances OXTR expression, OXTR signalling, or signalling downstream of the OXTR.

In particular, the OXTR agonist may be a small molecule, a nucleic acid molecule interfering specifically with OXTR expression, bait-substrates, dominant-negative mutants of OXTR, and aptamers or antibodies directed against OXTR.

In particular, the OXTR agonist may include oxytocin and analogues thereof. Examples of OXTR agonists, and in particular of oxytocin analogues, are disclosed in WO 2016/025629, U.S. Pat. No. 8,748,564, US2007117794 and US2013085106, and include for example demoxytocin, carbetocin, TC OT 39 and WAY-267464.

The following examples are given for purposes of illustration and not by way of limitation.

EXAMPLES

Example 1

Materials and Methods

Cell Source and Cell Culture

Healthy donor primary skeletal cells (Donor 1, Donor 3 and Donor 5) were Clonetics™ Human Skeletal Muscle Myoblasts (HSMM). In addition, cells from three DMD (Duchenne muscular dystrophy) donors (Donor Z, W and D1) and from a healthy donor (Donor A) were sourced.

Donor characteristics are detailed in table 1 below.

TABLE 1

Donor characteristics

|  | Donor 1 | Donor 3 | Donor 5 |
|---|---|---|---|
| Source | Lonza | Lonza | Lonza |
| Donor age (years) | 16 | 21 | 20 |
| Donor sex | Female | Male | Female |
| Donor race | Caucasian | Caucasian | Caucasian |
| Status | Healthy | Healthy | Healthy |
| Desmin positive cells | >90% | >90% | >90% |

|  | Donor Z | Donor W | Donor D1 | Donor A |
|---|---|---|---|---|
| Source | Hospital | Hospital | Hospital | Hospital |
| Donor age (years) | 3 | 1 | 1 | 1 |
| Donor sex | Male | Male | Male | Female |
| Donor race | Caucasian | Caucasian | Caucasian | Caucasian |
| Status | DMD deletion of exons 48 to 52 | DMD deletion of exons 46-52 | DMD duplication of exons 8 and 9 | Healthy |
| Desmin positive cells | 10% | 90% | 50% | >90% |

Muscle cells were maintained in culture following the supplier instructions with supplements and fetal bovine serum (FBS) serum provided by Lonza. An amplification step was performed in order to obtain enough cells for seeding the screening plates.

Hypertrophy Assay and Atrophy Rescue Assays

Hypertrophy and Atrophy Rescue assays were performed using an in vitro fully automated human myotube model called MyoScreen™ (Cytoo, France). This model relies on a tight control of the microenvironment that guides the differentiation of human primary myoblasts. Myotubes formed on MyoScreen™ micropatterns present a high level of maturation together with a highly standardized morphology.

Human primary myoblasts from donors were seeded in MyoScreen™ micropatterned 96-well plates (Cytoo, France), let them adhere for 24 h in growth medium, then run the differentiation in a low horse serum medium for at least 5 days.

At Day 0, MyoScreen™ plates (Cytoo, France) containing micropatterns were pre-filled with 200 µl/well of growth medium and stored in the incubator at 37° C. Human primary myoblasts were detached from the flasks, count, and seeded into the plates with 15 000 cells per well in 100 µl of growth medium.

At Day 1, the growth medium was changed for a differentiation medium, 300 µl/well (DMEM with 0.1% horse serum) in which myoblasts started differentiating and forming myotubes.

At Day 2, the differentiation medium was changed. Then candidate compounds were diluted with differentiation medium and transferred into the plate. The final concentration of DMSO should be not higher than 0.1%. At least 6 wells were treated with the vehicle as a basal control, and 6 wells were treated with IGF-1 at 100 ng/ml as positive hypertrophy control.

For Atrophy Rescue assay, one hour after candidate compound addition, atrophy inducers were added at the following final concentration: 150 ng/mL of myostatin, 25 ng/mL of IL-1β, 2 ng/mL of TNF-α, 0.5 ng/mL of TGF-β and 100 µM of dexamethasone.

At Day 6, cells were fixed with formalin 5% for 30 min at room temperature, then permeabilized with Triton X-100 at 0.1% in PBS for 15 min, and blocked with PBS+BSA 1% for 20 minutes. Myotubes were incubated with first antibody against Troponin T in blocking buffer for 1 h30, washed three times with PBS, incubated with secondary antibody and Hoescht (1/10000) for 1 h30, and washed three times with PBS.

Image Analysis

Images were acquired at 10× magnification with an Operetta High Content Imaging System. Image processing and analysis were performed with dedicated algorithms developed on the Acapella High Content Imaging Software (Perkin Elmer) by CYTOO. Eleven fields per well were acquired.

First, segmentation of myotubes and nuclei were done using respectively the Troponin T staining intensity and the Hoechst staining. One to two myotubes per micropattern were usually identified (a myotube is a troponin T staining area that includes at least 2 nuclei). The threshold of segmentation was set-up in order to avoid detecting the background noise and eliminate aberrant small myotube structures. At the end of this first step, specific readouts were calculated in the whole well, like the nuclei count and the fusion index (percentage of nuclei included in troponin T staining) Usually around 50 to 60 myotubes were detected per well in a control condition.

Then, an image clean-up step was performed on the Troponin T images in order to remove myotubes that touch the border of the image. The final valid myotubes were used to extract myotube morphology parameters including the myotube width and area, and the number of nuclei per myotube.

Nuclei Count, Fusion Index, Mean myotube Area and Number of nuclei per myotube have been validated as relevant and sensitive readouts of myotube differentiation as well as atrophic and hypertrophic induction.

Primary Screening

A primary screening was run to identify hypertrophy compounds that increase the myotube differentiation and size. Candidate compounds were tested at 10 µM in monoplicate on Donor 3 cells.

Retest

A retest was run, by cherry picking (same compound batch as primary screening): each hit was tested in the same conditions as in the Primary Screening (Donor 3, 10 µM) in six well replicates.

Dose Response on Three Healthy Donors

Dose response assays were performed on three healthy donors (Donors 3, 5 and 1): 8 doses of candidate compounds between 33 µM and 0.015 µM, 2 well replicates per dose.

$EC_{50}$ Calculation

Compounds of interest were tested several times in dose response, with triplicate of wells per dose. Results were normalized to the control condition (basal level), and plotted using GraphPad Prism. The readout "nuclei count" allowed detecting any toxicity effect. The readouts "fusion index" and "myosin area" were used to determine the $EC_{50}$ value using the GraphPad Prism fitting solution.

Atrophy Rescue Evaluation

Atrophy Rescue assays were performed in triplicate in the presence of atrophy inducers, i.e. TNF-α, IL-1β, Myostatin, TGF-β and dexamethasone.

Results

As shown on Table 2 below, RepSox was identified as skeletal muscle hypertrophy inducers during the primary screening and the retest, inducing an increase in the fusion index or/and myotube area readouts by more than +170%.

TABLE 2

Hypertrophy activity on the healthy donor 3

| Compounds | Primary screening (% Activity) | Retest (% Activity) |
|---|---|---|
| RepSox | 183 | 171 |
| IGF-1 (positive control) | 210 | 190 |

(% Activity = Myotube fusion index (compound) *100/Myotube Fusion index (basal control)

Dose responses were performed on three healthy donors. Results are presented in Table 3. RepSox was active on all donors.

TABLE 3

Results of the first dose response assay on different donors

| Compounds | Donor 3 % Activity | Donor 3 $EC_{50}$ | Donor 1 % Activity | Donor 1 $EC_{50}$ | Donor 5 % Activity | Donor 5 $EC_{50}$ |
|---|---|---|---|---|---|---|
| RepSox | 140 | 5 nM | 143 | 560 nM | 204 | 2.5 nM |
| IGF-1 | 178 | | 150 | | 185 | |

Furthermore 8 additional ALK5 inhibitors were tested, namely SB 525334, SD208, SB 505124, R268712, LY 364947, GW 788388, D 4476 and A 83-01. Results are shown in Table 4. $EC_{50}$ values below the micromolar range were confirmed.

TABLE 4

Results of the second dose response assay on the healthy donor 3

| Compounds | Donor 3 % Activity | Donor 3 $EC_{50}$ (nM) |
|---|---|---|
| SB 525334 | 142 | 3 |
| RepSox | 140 | 5 |
| SD208 | 138 | 65 |
| SB 505124 | 136 | <1 |
| R268712 | 132 | 1 |
| LY 364947 | 132 | 25 |
| GW 788388 | 130 | 88 |
| D 4476 | 128 | <1 |
| A 83-01 | 127 | 10 |
| IGF-1 | 178 | |

The activity of RepSox and GW 788388 was also assayed on cells from DMD donors, i.e. Donor Z, W and D1. Results are presented in Table 5.

TABLE 5

Hypertrophy activity on DMD donors

| Compounds | Donor Z (% Activity) | Donor W (% Activity) | Donor D1 (% Activity) |
|---|---|---|---|
| RepSox | 176 | 120 | 210 |
| GW 788388 | 196 | 118 | |
| IGF-1 (positive control) | 143 | 100 | 163 |

(% Activity = Myotube fusion index (compound) *100/Myotube Fusion index (basal control)

Atrophy rescue assays was performed for RepSox. Myotubes from the healthy donor 3 were atrophied using different inducers: TNF-α, IL-1β, Myostatin, TGF-β and dexamethasone. The ability of RepSox to block the atrophy induced by these different atrophy inducers was determined.

Results presented in Table 6 demonstrate that RepSox can inhibit the atrophy induced by IL-1β, TNF-α, Myostatin, TGF-β and dexamethasone.

TABLE 6

Results of atrophy rescue assays

| Compounds | IL-1 | TNF-alpha | Myostatin | TGF-β | dexamethasone |
|---|---|---|---|---|---|
| RepSox | ++ | ++ | +++ | +++ | +++ |
| IGF-1 | +++ | +++ | +++ | ++ | +++ |

(+++: total rescue, ++: partial rescue, + low rescue)

Example 2: Acetylcholine Receptor Clustering Assay

Materials and Methods

The MyoScreen™ protocol was performed as described in the Hypertrophy and Atrophy rescue assay described in Example 1 but was stopped at Day 9 instead of Day 6. At the end of the assay, AchR were immunostained using a specific antibody in addition to Troponin T and nuclei. Images were acquired at ×20 with an Operetta High Content Imaging System from Perkin Elmer. Image processing and analyses were performed with a dedicated algorithm developed on the Acapella High Content Imaging Software (Perkin Elmer). Specific readouts were calculated in each well: nuclei count and myotube fusion index, number of AchR, AchR mean area, AchR total area normalized by the myotube total area.

Results

Remarkably, when labeled with a specific anti-AChR antibody, MyoScreen myotubes at 6 days post-differentiation display AChR clusters punctuated along the sarcolemma membrane in the middle of the myotube fibre and in distinct regions at the ends of myotubes. To develop an automated AChR cluster assay, an AChR detection routine was developed that was sensitive and robust enough to analyze aggregate number and size clusters in images using the Operetta/Acapella system. The effect of RepSox on AchR clustering was evaluated to demonstrate the compound positive effect on neuro-muscular junction. After 8 days of differentiation that included 7 days of drug treatment, myotubes treated RepSox showed substantially more AChR clusters and total AChR area increased by 6-fold, while IGF-1 had no effect (FIG. 1).

Example 3: Calcium Flux Assay

Materials and Methods

Cells were washed with calcium buffer containing (in mM): 130 NaCl, 5.4 KCl, 1.8 CaCl2, 0.8 MgCl2, 5.6 D-glucose, 10 Hepes, pH 7.4. Cells were then incubated for 1 h with 2 μM Fluo-4 AM (F14201-Invitrogen) in an incubator (37° C., 5% CO2). After washing to remove unloaded dye, myotube responses to 20 μM ACh (A6625-Sigma-Aldrich), were videoimaged. Stream acquisitions were set at 1 sec intervals and one field of view was acquired per well. Images were processed and analyzed automatically using a dedicated software developed in-house integrating the open-source ImageJ framework. The image analysis tool segments the myotubes in images acquired in the same well. The Fluo-4 total fluorescence intensity was measured inside each myotube and corrected for background. The total intensity was normalized to the myotube area to obtain the mean fluorescence intensity readout. For data presentation, fluorescence intensities (F) were normalized to the mean intensity of the three first time points (F/F0).

Results

Figure 2:
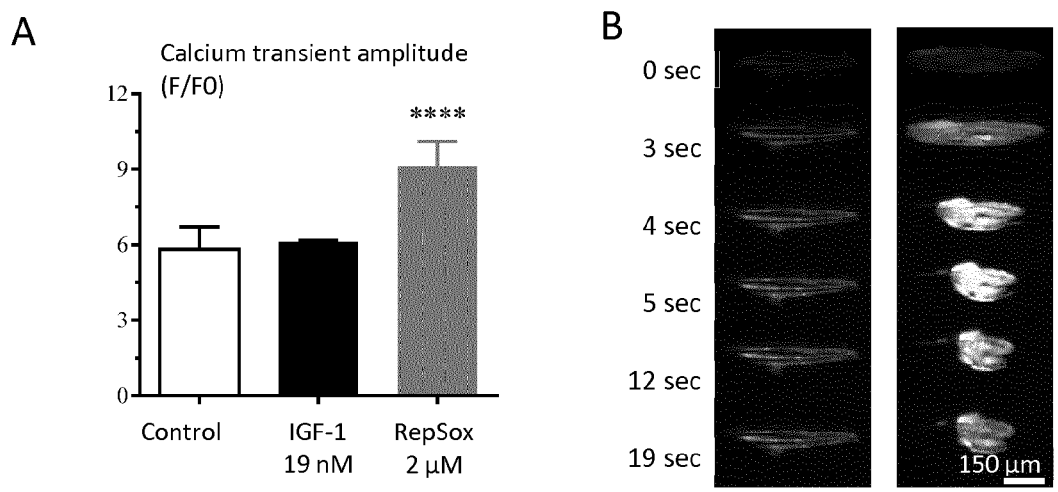
FIG. 2: RepSox activity on calcium flux. A: Mean peak amplitudes of Fluo-4 fluorescence in 20 μM ACh-stimulated myotubes differentiated for 8 days of which 7 days were in the presence of IGF-1, or RepSox. n=2-5 wells; ****p≤0.0001 versus control myotubes by Mann-Whitney analysis. B: Representative pseudo-colour images extracted from a calcium flux experiment showing levels of intracellular free Ca2+ in myotubes before (0 sec) and after stimulation with ACh (3 to 19 sec).

Interestingly, in the case of Ca2+ flux measurements after ACh stimulation, only myotubes differentiated in the presence of RepSox showed a statistically significant increase of 1.56-fold in [Ca2+]i peak amplitude compared to control myotubes. Again, IGF-1 had no effect. Calcium flux timelapse videos also implied that myotubes differentiated in the presence of RepSox displayed a marked increase in the number of retracting myotubes after ACh stimulation (FIG. 2).

Example 4: Contractile Activity Assay

Materials and Methods

Cells were washed with calcium buffer as above. Myotube contraction was induced by addition of 100 μM ACh for 3 mins after which myotubes were fixed and immunostained with troponin T antibody. Automated acquisition was performed on the Operetta platform with a x10/0.3 NA objective. Detaching myotubes were automatically detected and quantified using Acapella, based on the detection of high intensity regions within the edges of segmented myotubes that mark the spots where the myotubes detached.

Results

Figure 3:
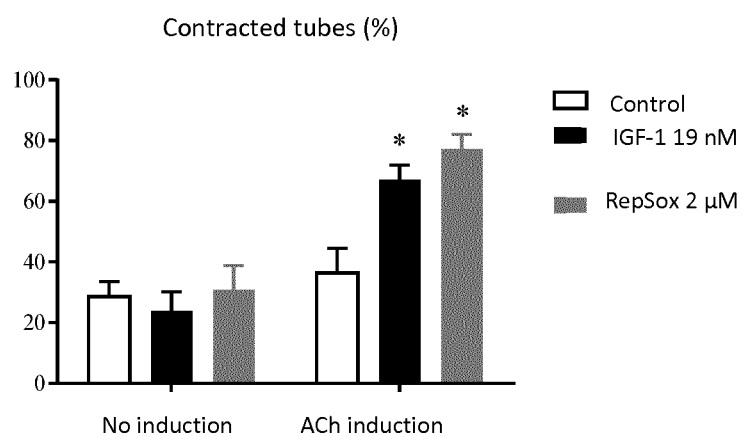
FIG. 3: RepSox activity on contraction. Treatment of differentiating myotubes for 96 h with 2 μM RepSox significantly increased the percentage of myotubes that exhibit strong contractions, detected as myotubes retracted from the micropattern when stimulated with 100 μM ACh. n=4 wells; *p≤0.05 versus control myotubes by Mann-Whitney analysis.
Figure 4:
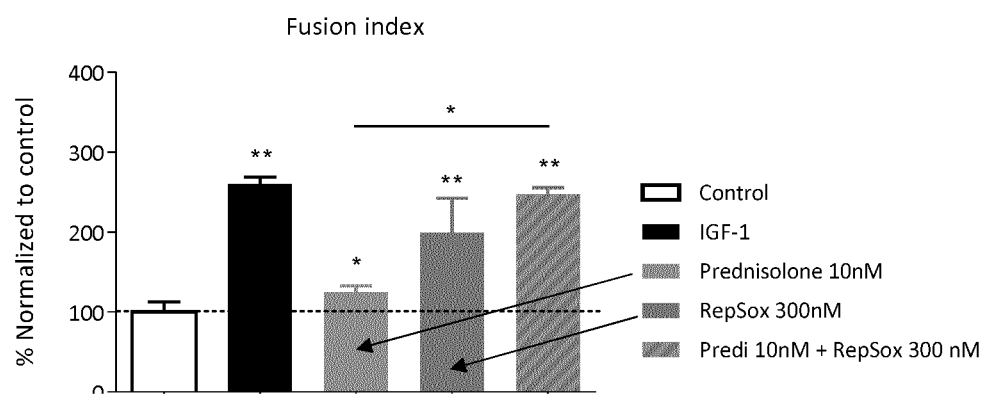
FIG. 4: Fusion index obtained with prednisolone, RepSox and the combination of prednisolone and RepSox.

The effect on contraction force was quantified after 5 days of differentiation that included 4 days of RepSox or IGF-1 treatment. When stimulated by addition of 100 μM ACh, active contractile force augmented in in myotubes treated with RepSox (77±5%) and IGF-1 (67±5%). RepSox enhances ACh-stimulated [Ca2+]i influx and contraction force (FIG. 3).

Example 5: Combinations ALK5 Inhibitor and Glucocorticoid

Materials and Methods

The hypertrophy assay was performed as described in Example 1 on Donor Z, a DMD donor. The treatment was performed at Day 2, adding prednisolone at 10 nM, RepSox or GW788388 at 300 nM, or a combination of prednisolone and one of these two ALK5 inhibitors. After 4 days of treatment, the myotube fusion index and mean area were measured by image analysis as described in in the Material and Method of Example 1.

Results

As shown in FIGS. 4 to 7, the positive control IGF-1 increases both the Fusion index (+160%) and the Myotube mean area (+54%), validating the hypertrophy assay on the DMD Donor Z.

The ALK5 inhibitors RepSox and GW788388 both induces a significant hypertrophy when added alone at 300 nM. Note than RepSox is the most potent ALK5 inhibitor, increasing the Fusion index by +100% (vs +41% with GW788388) and the Myotube Area by +68% (vs +21% with GW788388).

Prednisolone alone at 10 nM induces a low increase in the Donor Z myotubes Fusion index (+25%), but does not enhance significantly the Myotube mean area.

Figure 5:
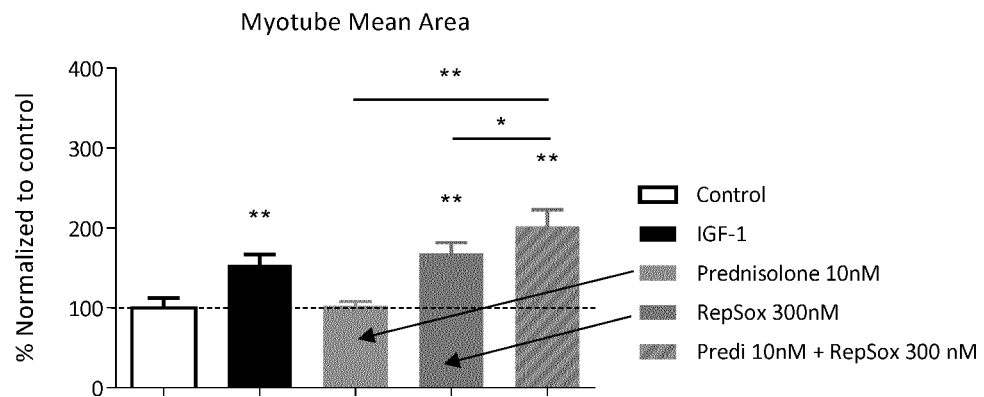
FIG. 5: Myotube mean area obtained with prednisolone, RepSox and the combination of prednisolone and RepSox.
Figure 6:
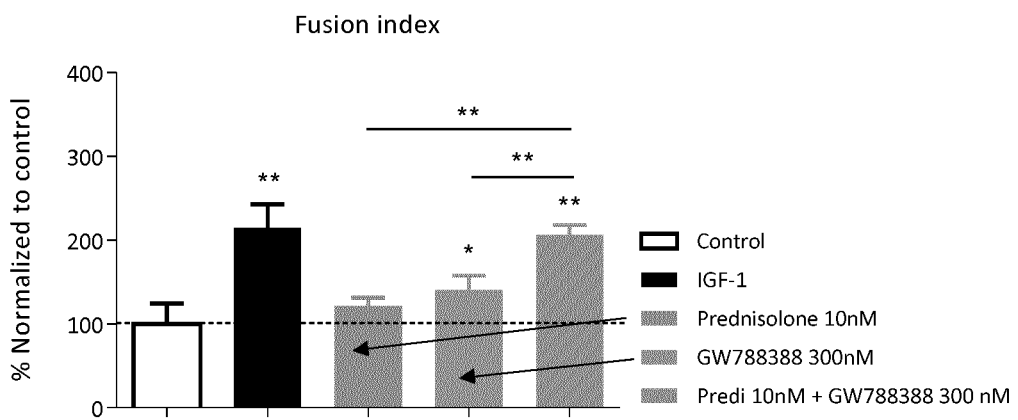
FIG. 6: Fusion index obtained with prednisolone, GW788388 and the combination of prednisolone and GW788388.
Figure 7:
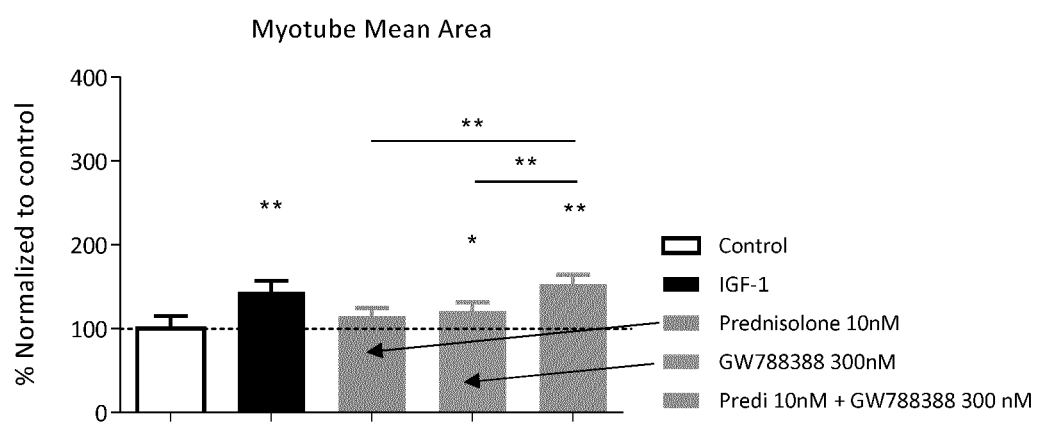
FIG. 7: Myotube mean area obtained with prednisolone, GW788388 and the combination of prednisolone and GW788388.

The combination of one ALK5 inhibitor and prednisolone potentiates the effect of each one alone: both the Fusion index and Myotube area are significantly higher in the combination condition than in each compound treatment. For example, the combination of prednisolone and RepSox leads to an increase in the Fusion index by +148% (FIG. 4) and in the Myotube area by +102% (FIG. 5).

Example 6: Electrical Pulse Stimulation Assay

Material and Method

Myotubes from Donors 5 and A (cf. table 1) were differentiated for 6 to 7 days including 5 to 6 days of treatment with RepSox at 3 to 500 nM. Cells were washed with calcium buffer containing (in mM): 130 NaCl, 5.4 KCl, 1.8 CaCl$_2$, 0.8 MgCl$_2$, 5.6 D-glucose, 10 Hepes, pH 7.4. Cells were then incubated for 1 h with 2 μM Fluo-4 AM (F14201-Invitrogen) in an incubator (37° C., 5% CO2). After washing to remove unloaded dye, myotube responses to electrical stimulation pulses were monitored using the FDSS/μCELL/EFS from Hamamatsu Photonics. Twitch stimulations were run at 0.2 Hz with pulse width 50 ms 5V for 60 seconds. Tetanus stimulation was run at 30 Hz with pulse width 15 ms 3V for 20 seconds. The Fluo-4 total fluorescence intensity is measured in each well. For data presentation, fluorescence intensities (F) were normalized to the mean intensity of the first timepoints (F/F0).

Results

Figure 8A:
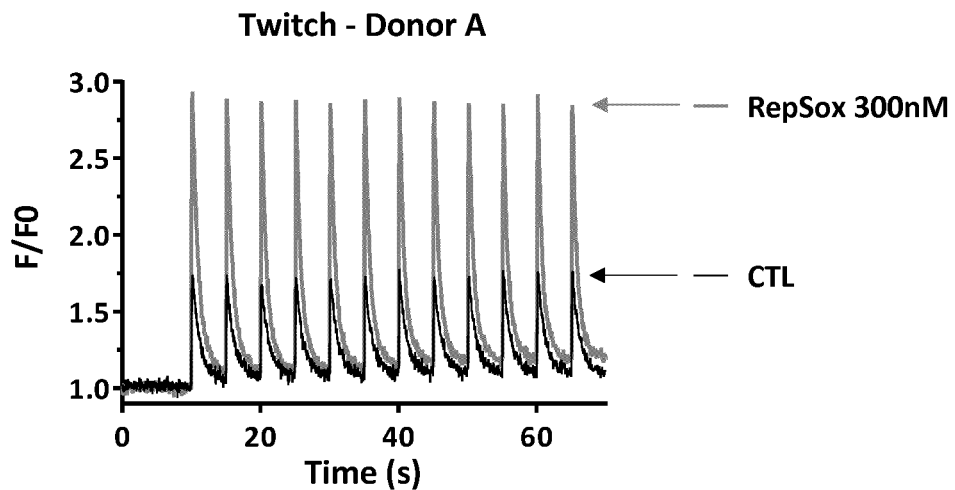
FIG. 8: Response of myotubes from Donors A (A) and 5 (B) to repeated twitch electrical stimulations. Fluorescence intensities (F) were normalized to the mean intensity of the first timepoints (F/F0).
Figure 8B:
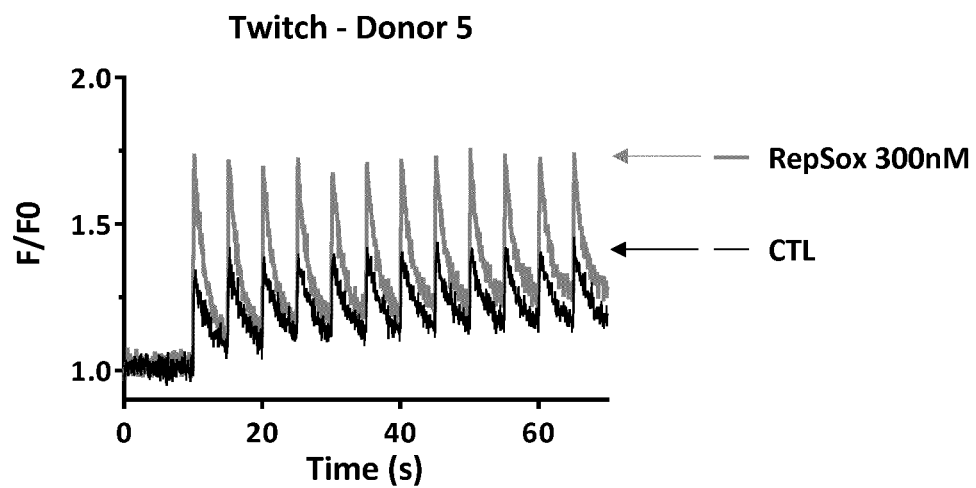

Myotubes from Donor A and Donor 5 responded to repeated twitch electrical stimulations as shown in FIGS. 8A and 8B. The calcium peak amplitude is twice higher when myotubes are treated with RepSox 300 nM for 5 days.

Figure 9A:
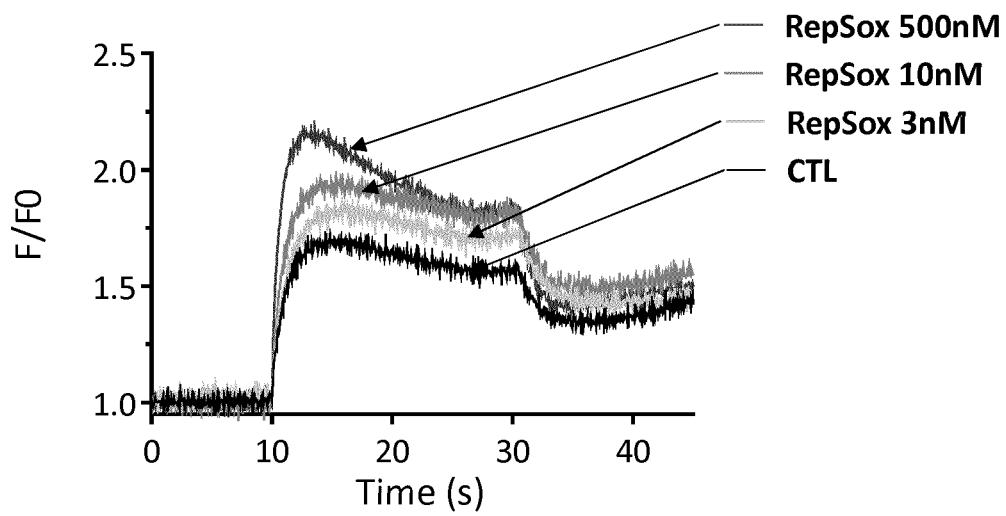
FIG. 9: Tetanus response of myotubes from Donor 5 (A). Fluorescence intensities (F) were normalized to the mean intensity of the first timepoints (F/F0). RepSox-treated myotubes tetanus response increases with RepSox concentrations leading to significant differences with Control myotubes. *p≤0.05 and ***p≤0.001 versus control myotubes by Mann-Whitney analysis.
Figure 9B:
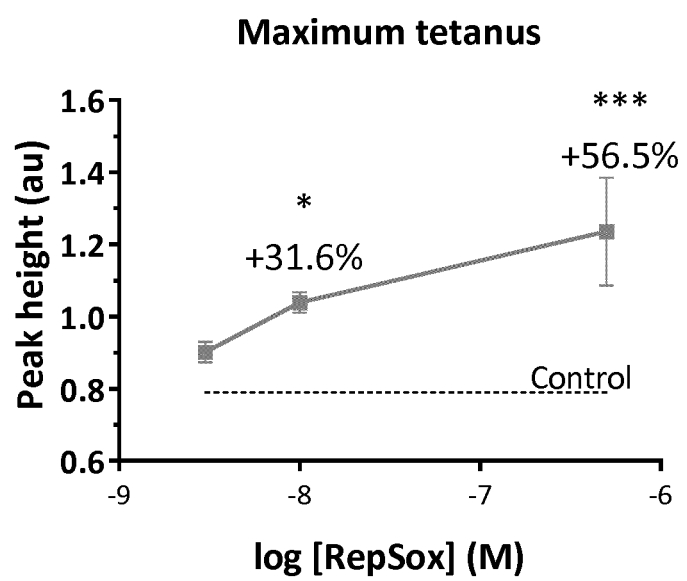

Increasing stimuli frequency results in wave summation and finally complete tetanus reflecting in vivo phenomenon (FIG. 9A). RepSox-treated myotubes tetanus response increases with RepSox concentrations leading to significant differences with Control myotubes (FIG. 9B).

These results confirm that RepSox enhances the myotube calcium flux after chemical (ACh) or electrical stimulations (FDSS/μCELL/EFS).

The invention claimed is:

1. A method of treating a neuromuscular junction disease, comprising the administration of an ALK5 inhibitor, optionally in combination with a glucocorticoid to a subject in need thereof, wherein the ALK5 inhibitor is not used in combination with an oxytocin receptor agonist, and wherein the ALK5 inhibitor is selected from the group consisting of RepSox and pharmaceutically acceptable salts, hydrates or solvates thereof.

2. The method according to claim 1, wherein the ALK5 inhibitor and, optionally, the glucocorticoid are administered in the form of a pharmaceutical composition comprising a pharmaceutical acceptable excipient.

3. The method according to claim 1, wherein the ALK5 inhibitor is administered in combination with a glucocorticoid that is selected from the group consisting of prednisolone, prednisone, cortisone, corticosterone, hydrocortisone, fludrocortisone, fluorometholone, deoxycorticosterone, ketoconazole, budesonide, methylprednisolone, fluticasone, clobetasol, clobetasone, fluocinolone, flunisolide, mometasone, prednicarbate, amcinonide, diflucortolone, beclomethasone, betamethasone, dexamethasone, triamcinolone, deflazacort, and pharmaceutically acceptable salts, hydrates, solvates or prodrugs thereof.

4. The method according to claim 1, wherein the neuromuscular junction disease is selected from the group consisting of myasthenia gravis, autoimmune neuromyotonia (Isaacs' syndrome), Lambert-Eaton myasthenic syndrome, and a neuromuscular junction disease resulting from a form of poison that affects neuromuscular junction functioning.

5. The method according to claim 1, wherein the ALK5 inhibitor and the glucocorticoid are administered in the form of a pharmaceutical composition comprising a pharmaceutical acceptable excipient.

* * * * *